(12) United States Patent
Seifert et al.

(10) Patent No.: US 7,744,583 B2
(45) Date of Patent: Jun. 29, 2010

(54) SYSTEMS AND METHODS OF DE-ENDOTHELIALIZATION

(75) Inventors: Paul S. Seifert, Oregon House, CA (US); Elaine Lee, Sunnyvale, CA (US); Michael P. Wallace, Fremont, CA (US); Stephen C. Porter, Oakland, CA (US)

(73) Assignee: Boston Scientific Scimed, Maple Grove, MN (US)

( * ) Notice: Subject to any disclaimer, the term of this patent is extended or adjusted under 35 U.S.C. 154(b) by 1704 days.

(21) Appl. No.: 10/357,572

(22) Filed: Feb. 3, 2003

(65) Prior Publication Data

US 2004/0153120 A1 Aug. 5, 2004

(51) Int. Cl.
*A61M 31/00* (2006.01)
(52) U.S. Cl. .................. 604/507; 604/508; 604/509
(58) Field of Classification Search ............ 604/500, 604/48, 113, 511, 506, 507, 513, 518, 508, 604/509; 128/898; 606/200, 213
See application file for complete search history.

(56) References Cited

U.S. PATENT DOCUMENTS

| | | | |
|---|---|---|---|
| 3,174,851 A | 3/1965 | Buehler et al. | |
| 3,351,463 A | 11/1967 | Rozner et al. | |
| 3,753,700 A | 8/1973 | Harrison et al. | |
| 4,655,771 A | 4/1987 | Wallsten | |
| 4,735,201 A * | 4/1988 | O'Reilly | 606/28 |
| 4,850,960 A | 7/1989 | Grayzel | |
| 4,865,516 A | 9/1989 | Focke et al. | |
| 4,954,126 A | 9/1990 | Wallsten | |
| 4,994,069 A | 2/1991 | Ritchart et al. | |
| 5,053,006 A * | 10/1991 | Watson | 604/20 |
| 5,108,407 A * | 4/1992 | Geremia et al. | 606/108 |
| 5,151,105 A | 9/1992 | Kwan-Gett | |
| 5,176,661 A | 1/1993 | Evard et al. | |
| 5,203,772 A | 4/1993 | Hammerslag et al. | |
| 5,234,437 A | 8/1993 | Sepetka | |
| 5,250,071 A | 10/1993 | Palermo | |
| 5,261,916 A | 11/1993 | Engelson | |
| 5,273,751 A * | 12/1993 | Dubroff | 424/427 |
| 5,290,552 A | 3/1994 | Sierra et al. | |

(Continued)

FOREIGN PATENT DOCUMENTS

WO    WO 01/45572    6/2001

(Continued)

OTHER PUBLICATIONS

PCT International Search Report for PCT/US2003/38464, Applicant: Scimed Life Systems, Inc., Forms PCT/ISA/210 and 220, dated Sep. 1, 2004 (7 pages).

*Primary Examiner*—Kevin C Sirmons
*Assistant Examiner*—Michael J Anderson
(74) *Attorney, Agent, or Firm*—Vista IP Law Group LLP

(57) ABSTRACT

Apparatus and methods for treating a wall of an aneurysm formed in a vessel includes introducing a tubular member into the body lumen until a distal end of the tubular member is located within the aneurysm. A fluid is delivered via a lumen of the tubular member into the aneurysm to at least partially de-endothelialize the wall of the aneurysm, thereby causing an endothelium of the wall to generate fibrous tissue to strengthen the wall of the aneurysm.

34 Claims, 16 Drawing Sheets

U.S. PATENT DOCUMENTS

| | | | |
|---|---|---|---|
| 5,304,194 A | 4/1994 | Chee et al. | |
| 5,304,195 A | 4/1994 | Twyford, Jr. et al. | |
| 5,312,415 A | 5/1994 | Palermo | |
| 5,350,397 A | 9/1994 | Palermo et al. | |
| 5,363,861 A | 11/1994 | Edwards et al. | |
| 5,368,566 A * | 11/1994 | Crocker | 604/101.02 |
| 5,405,379 A | 4/1995 | Lane | |
| 5,423,829 A | 6/1995 | Pham et al. | |
| 5,522,836 A | 6/1996 | Palermo | |
| 5,582,619 A | 12/1996 | Ken | |
| 5,624,461 A | 4/1997 | Mariant | |
| 5,639,277 A | 6/1997 | Mariant et al. | |
| 5,649,949 A | 7/1997 | Wallace et al. | |
| 5,690,666 A | 11/1997 | Berenstein et al. | |
| 5,713,917 A | 2/1998 | Leonhardt et al. | |
| 5,718,711 A | 2/1998 | Berenstein et al. | |
| 5,749,894 A * | 5/1998 | Engelson | 606/213 |
| 5,792,154 A | 8/1998 | Doan et al. | |
| 5,820,581 A * | 10/1998 | Wolfinbarger, Jr. | 604/500 |
| 5,826,587 A | 10/1998 | Berenstein et al. | |
| 5,843,111 A | 12/1998 | Sepetka et al. | |
| 5,843,156 A * | 12/1998 | Slepian et al. | 128/898 |
| 5,851,206 A * | 12/1998 | Guglielmi et al. | 606/28 |
| 5,893,847 A | 4/1999 | Kordis | |
| 5,916,235 A * | 6/1999 | Guglielmi | 606/200 |
| 5,919,187 A * | 7/1999 | Guglielmi et al. | 606/32 |
| 5,925,038 A | 7/1999 | Panescu et al. | |
| 5,928,260 A | 7/1999 | Chin et al. | 606/200 |
| 6,024,095 A | 2/2000 | Stanley, III | 128/898 |
| 6,048,333 A * | 4/2000 | Lennox et al. | 604/113 |
| 6,096,021 A * | 8/2000 | Helm et al. | 604/509 |
| 6,146,373 A | 11/2000 | Cragg et al. | |
| 6,168,788 B1 | 1/2001 | Wortham | |
| 6,216,044 B1 | 4/2001 | Kordis | |
| 6,221,066 B1 | 4/2001 | Ferrera et al. | |
| 6,244,610 B1 | 6/2001 | Kramer-Massow | |
| 6,277,126 B1 | 8/2001 | Barry et al. | |
| 6,280,457 B1 | 8/2001 | Wallace et al. | |
| 6,287,318 B1 | 9/2001 | Villar et al. | |
| 6,322,576 B1 | 11/2001 | Wallace et al. | |
| 6,371,972 B1 | 4/2002 | Wallace et al. | |
| 6,375,668 B1 * | 4/2002 | Gifford et al. | 606/200 |
| 6,409,721 B1 | 6/2002 | Wheelock et al. | |
| 6,416,541 B2 | 7/2002 | Denardo | |
| 6,423,085 B1 | 7/2002 | Murayama et al. | |
| 6,425,914 B1 | 7/2002 | Wallace et al. | |
| 6,456,127 B1 | 9/2002 | Tsecouras | |
| 6,463,317 B1 * | 10/2002 | Kucharczyk et al. | 600/411 |
| 6,468,266 B1 | 10/2002 | Bashiri et al. | |
| 6,475,227 B2 | 11/2002 | Burke et al. | |
| 6,478,773 B1 | 11/2002 | Gandhi et al. | |
| 6,494,884 B2 | 12/2002 | Gifford, III et al. | |
| 6,500,149 B2 | 12/2002 | Gandhi et al. | |
| 6,746,468 B1 * | 6/2004 | Sepetka et al. | 606/200 |
| 6,827,701 B2 * | 12/2004 | MacMahon et al. | 604/38 |
| 7,530,976 B2 * | 5/2009 | MacMahon et al. | 604/508 |
| 2002/0143349 A1 * | 10/2002 | Gifford et al. | 606/157 |
| 2002/0169420 A1 | 11/2002 | Galt et al. | |
| 2002/0169473 A1 * | 11/2002 | Sepetka et al. | 606/200 |
| 2002/0183684 A1 | 12/2002 | Dev et al. | |
| 2002/0183692 A1 * | 12/2002 | Callister | 604/113 |
| 2003/0004568 A1 * | 1/2003 | Ken et al. | 623/1.46 |
| 2003/0060863 A1 * | 3/2003 | Dobak, III | 607/104 |
| 2003/0204246 A1 * | 10/2003 | Chu et al. | 623/1.23 |
| 2005/0085769 A1 * | 4/2005 | MacMahon et al. | 604/96.01 |
| 2006/0034769 A1 * | 2/2006 | Kohn et al. | 424/9.45 |

FOREIGN PATENT DOCUMENTS

| | | |
|---|---|---|
| WO | WO 02/096301 | 12/2002 |

\* cited by examiner

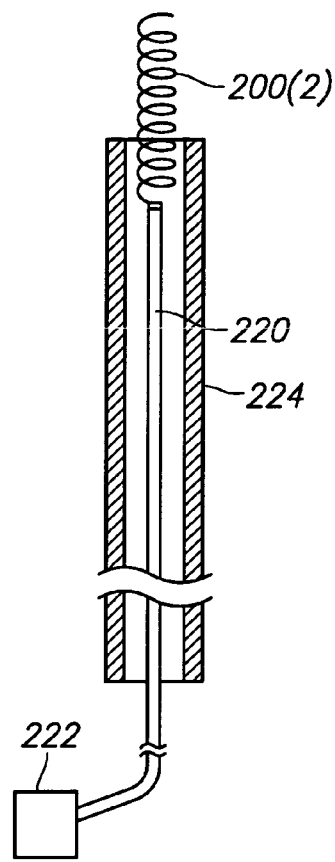
FIG. 29A
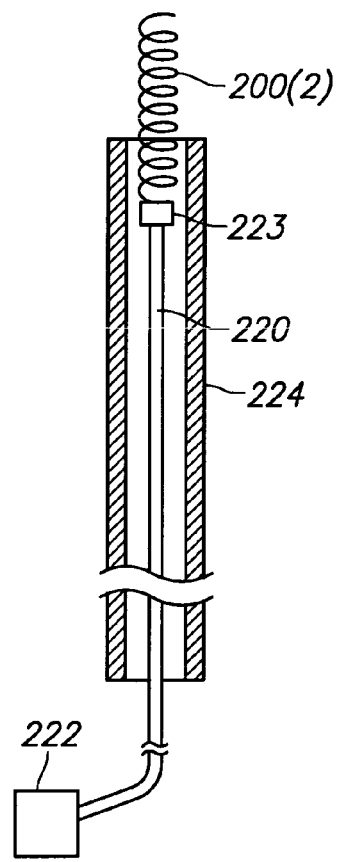
FIG. 29B
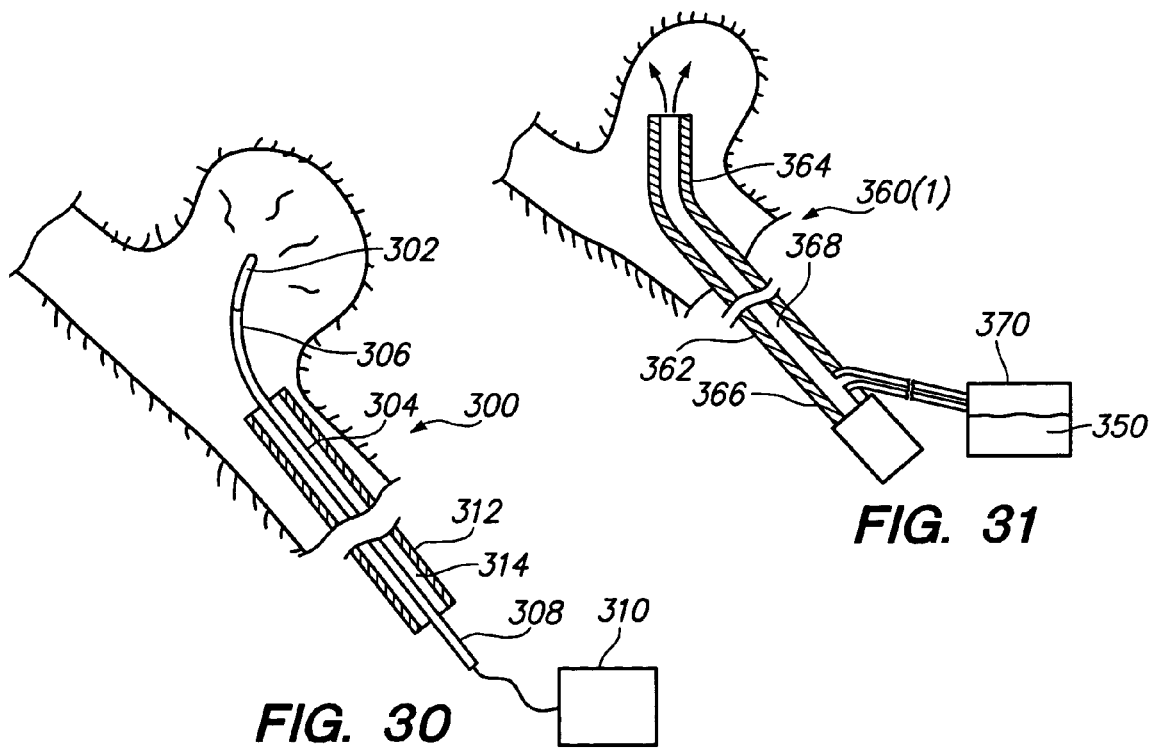
FIG. 30
FIG. 31

SYSTEMS AND METHODS OF DE-ENDOTHELIALIZATION

FIELD OF THE INVENTION

The field of the invention pertains to embolizing blood vessels or aneurysms, and more particularly, to systems and methods for reducing blood vessel or aneurysm recanalization.

BACKGROUND

In many clinical situations, blood vessels are occluded for a variety of purposes, such as to control bleeding, to prevent blood supply to tumors, to stop blood flow to arterio-venous malformations or fistulas, and to block blood flow within an aneurysm.

Embolization of blood vessels is particularly useful in treating aneurysms. Aneurysms are abnormal blood-filled dilations of a blood vessel wall that may rupture causing significant bleeding. For the cases of intracranial aneurysms, the significant bleeding may lead to damage to surrounding brain tissue or death. Intracranial aneurysms may be difficult to treat when they are formed in remote cerebral blood vessels, which are very difficult to access. If left untreated, hemodynamic forces of normal pulsatile blood flow can rupture fragile tissue in the area of the aneurysm causing a stroke.

Vaso-occlusive devices have been used to treat aneurysms. Vaso-occlusive devices are surgical implants placed within blood vessels or vascular cavities, typically using a catheter, to form a thrombus and occlude the site. For instance, a stroke or other such vascular accident may be treated by placing a vaso-occlusive device proximal of the site to block the flow of blood to the site and alleviate the leakage. An aneurysm may similarly be treated by introducing a vaso-occlusive device through the neck of the aneurysm. The thrombogenic properties of the vaso-occlusive device cause a mass to form in the aneurysm and alleviate the potential for growth of the aneurysm and its subsequent rupture. Other diseases, such as tumors, may often be treated by occluding the blood flow to the tumor.

There are a variety of vaso-occlusive devices suitable for forming thrombi. One such device is found in U.S. Pat. No. 4,994,069, to Ritchart et al., the entirety of which is expressly incorporated by reference herein. That patent describes a vaso-occlusive coil that assumes a linear helical configuration when stretched and a folded convoluted configuration when relaxed. The stretched configuration is used to deliver the coil to the desired site and the convoluted configuration occurs when the coil is ejected from the catheter and the coil relaxes. Ritchart et al. describes a variety of shapes, including "flower" shapes and double vortices. A random shape is described as well.

U.S. Pat. No. 6,280,457B1 to Wallace et al., describes an occlusive device comprising an inner core wire covered with a polymer. The polymeric material includes protein based polymers, absorbable polymers, non-protein based polymers, and combinations thereof. The polymer may contribute to forming emboli for occluding a body cavity.

Vaso-occlusive coils having complex, three-dimensional structures in a relaxed configuration are described in U.S. Pat. No. 6,322,576B1 to Wallace et al. The coils may be deployed in the approximate shape of a sphere, an ovoid, a clover, a box-like structure or other distorted spherical shape. The patent also describes methods of winding the anatomically shaped vaso-occlusive device into appropriately shaped forms and annealing them to form various devices.

Vaso-occlusive coils having little or no inherent secondary shape have also been described. For instance, co-owned U.S. Pat. Nos. 5,690,666 and 5,826,587 by Berenstein et al., describe coils having little or no shape after introduction into the vascular space.

Vaso-occlusive devices work initially by slowing blood flow inside the aneurysm. As a result of the slowed blood flow, the blood inside the aneurysm clots. The combination of the vaso-occlusive devices and the clot protects the aneurysm from hemodynamic forces (i.e., forces on the aneurysm wall due to blood flow) that may cause recanalization and recurrence of the aneurysm. However, recanalization and recurrence of the aneurysm may still occur for various reasons. For example, the vaso-occlusive device may rearrange itself due to the hemodynamic forces. Typically, the vaso-occlusive device(s) near the neck of the aneurysm is most affected by the effects of blood flow. Also, the clot formed may break down due to the hemodynamic forces and/or natural chemical processes. This is more likely to occur if the aneurysm is loosely packed with vaso-occlusive devices.

Accordingly, devices and methods for reducing recanalization or recurrence of an aneurysm would be useful.

SUMMARY OF THE INVENTION

The present invention is directed to apparatus and methods for treating aneurysms or other body cavities. More particularly, the present invention is directed to apparatus and methods for disrupting the endothelium of the wall of an aneurysm to reduce the risk of the wall expanding, thinning, and/or or rupturing, or to reduce the risk of recanalization of a body cavity, such as an arterio-venous malformation, fistula, or other blood vessel.

In accordance with one aspect of the present invention, an apparatus for disrupting an endothelium of an aneurysm or other body lumen wall is provided. Generally, the apparatus includes an elongate member including a proximal end and a distal end configured for insertion into a body lumen of a patient. The distal end of the elongate member may have a primary shape, e.g., a substantially linear relaxed shape, a curvilinear relaxed shape, and/or a helical coil shape. Optionally, the elongate member may have a secondary shape, e.g., a three-dimensional shape towards which the elongate member may be biased in a relaxed state free from external forces. The elongate member may be formed from an elastic or superelastic material and/or a bioabsorbable material.

Any of the apparatus described herein may include a delivery device, e.g., a sheath, catheter or other tubular member, for delivering the elongate member. For example, the distal end of the elongate member may be disposed within a lumen of the tubular member as a distal end of the tubular member is advanced to a treatment site, e.g., to prevent the distal end from contacting tissue prematurely, i.e., until deployed.

Optionally, the distal end of the elongate member may be deployable such that the distal end may remain within the aneurysm or other body cavity upon completing the procedure. The distal end of the elongate member may be deployable using a mechanical joint, an electrolytic joint, and/or a dissolvable adhesive. In addition or alternatively, the distal end of the elongate member may be steerable, e.g., to guide the distal end around bends, into a body cavity, such as an aneurysm sac, and/or otherwise manipulating the distal end during a procedure.

In one embodiment, one or more abrasive elements are carried on the distal end of the elongate member for disrupting the endothelium of the aneurysm or other body cavity. The abrasive element(s) may include hooks, needles, fins, saw tooth elements, and/or sharp particles. The abrasive element(s) that may be disposed on an entire exposed surface of the distal end of the elongate member or may be selectively disposed in a pattern on only a portion of the distal end. Preferably, the abrasive element(s) has(have) a size and stiffness for disrupting the endothelium of a vessel wall, e.g., a wall of an aneurysm, without substantial risk of penetrating completely through the wall.

Optionally, an expandable member may be carried by the distal end of the elongate member, the abrasive elements being carried on the expandable member. For example, the expandable member may be an expandable basket including one or more splines, each carrying one or more abrasive elements. Alternatively, the expandable member may be an elastic or inelastic balloon that may be expanded upon introducing fluid into an interior of the balloon. If the elongate member includes an expandable member, the expandable member may be collapsed when disposed within a delivery device, e.g., a sheath or other tubular member. The expandable member may be biased to expand towards an expanded configuration when deployed from the delivery device or may be controllably expanded, e.g., mechanically or using a fluid. In addition, the balloon may be porous and/or may include one or more openings or lumens for delivering a fluid, e.g., a de-endothelialization fluid beyond an outer surface of the balloon, as explained further below.

An apparatus, such as those described above, may be used for de-endothelializing an aneurysm. Initially, an apparatus may be provided that includes an elongate member carrying one or more abrasive elements on its distal end. The distal end may be introduced into a body lumen, e.g., a patient's vasculature, and advanced until the distal end reaches a target site intended for treatment, e.g., an aneurysm within a cerebral or other artery. The distal end may be provided within a catheter or other delivery device to protect the vasculature from being damaged by the abrasive elements and/or to protect the distal end of the elongate member.

For example, a delivery catheter may be positioned adjacent an aneurysm, and the distal end of the elongate member may be advanced from a lumen of the catheter into the aneurysm. The distal end of the elongate member may be manipulated, e.g., advanced, retracted, steered, and/or rotated to engage the abrasive elements with the wall of the aneurysm to disrupt the endothelium of the wall. If an expandable member is carried on the distal end, the expandable member may be expanded to enhance engaging the endothelium with the abrasive elements. Consequently, the patient's body may react to the disruption by generating fibrous tissue, e.g., scar tissue, that may thicken or otherwise strengthen the wall of the aneurysm, thereby substantially reducing the risk of the wall thinning further and/or the aneurysm growing or rupturing.

The elongate member may then be retracted into the catheter and both removed from the patient. Alternatively, the distal end of the elongate member may be released from the elongate member to at least partially fill the aneurysm.

In accordance with another aspect of the present invention, another apparatus for disrupting an endothelium of an aneurysm or other body cavity wall is provided that uses thermal energy to disrupt the endothelium. Similar to the previous embodiments, the apparatus may include an elongate member having a distal end, which may be steerable and/or deployable, as described above. A thermal element may be carried by the distal end of the elongate member that is configured for being heated or cooled to a de-endothelializing temperature. Similar to the previous embodiment, the distal end may include an expandable member, e.g., an expandable basket or balloon, that may carry the heating or cooling element.

In one form, the thermal element may be an electrically resistive heating element that may be coupled to a source of electrical energy. Upon delivering electrical energy to the distal end, the resistive heating element may become heated sufficiently to disrupt the endothelium that it contacts directly or that is heated by conduction and/or convection. Alternatively, the thermal element may be an energy storage element that may be heated or cooled before being inserted through a thermally insulated delivery device, e.g., a sheath, that has been placed adjacent the aneurysm.

In a further alternative, the thermal element may be an expandable balloon or other hollow element. The hollow element may be filled with a heated or cooled fluid to heat or cool the hollow element to a desired temperature for de-endothelializing the wall of an aneurysm that it contacts directly or to which it is coupled by conduction or convection. Optionally, the hollow element may include one or more openings such that the heated or cooled fluid may be delivered from the hollow element into the aneurysm or body cavity to disrupt the endothelium of the wall. In this embodiment, the elongate member and/or the delivery device may include a sealing member that may be used to at least partially seal the aneurysm or a body lumen communicating with the aneurysm.

These embodiments may be used to disrupt the endothelium of an aneurysm or other body cavity wall using thermal energy. The distal end of the elongate member may be advanced from a delivery device, such as a sheath or catheter, into the aneurysm. For example, the delivery device may be advanced through the patient's vasculature with the elongate member therein. Once the delivery device is adjacent to the aneurysm, the distal end of the elongate member may be advanced from the delivery device to place the thermal element within the aneurysm.

If the thermal element includes an electrically resistive heating element, electrical energy may be delivered to the heating element, thereby heating the interior of the aneurysm and/or heating the wall contacted by the heating element until the endothelium is disrupted. Alternatively, if the thermal element includes an expandable member, the expandable member may be expanded within the aneurysm to at least partially fill the aneurysm cavity.

In addition or alternatively, if the thermal element is porous or includes outlet ports coupled to a source of heated or cooled fluid via a lumen, the fluid may be delivered into the aneurysm to disrupt the endothelium. Optionally, a sealing member may be located proximal to the thermal element that may be expanded or otherwise engaged with the neck of the aneurysm to substantially seal the aneurysm. This may prevent fluid delivered into the aneurysm from escaping into adjacent body lumen(s). Preferably, the fluid is heated to a temperature above fifty degrees Celsius (50° C.) or cooled to a temperature below zero degrees Celsius (0° C.).

In accordance with yet another aspect of the present invention, a method is provided for treating a wall of an aneurysm, arterio-venous malformation, fistula, or other a body lumen. A tubular member may be introduced into the vasculature until a distal end of the tubular member is located within the aneurysm or blood vessel. A fluid may be delivered via a lumen of the tubular member into the aneurysm or blood vessel to at least partially de-endothelialize the wall of the aneurysm or blood vessel. This may cause an endothelium of the wall to generate fibrous tissue to strengthen the wall of the aneurysm or to strengthen and/or occlude the blood vessel.

In one embodiment, a sealing member may be carried by one of the inner and outer members, and the sealing member may be engaged with a neck of the aneurysm to substantially sealing the aneurysm before the fluid is delivered into the aneurysm. In an exemplary embodiment, the sealing member may include an annular shaped member including an outer wall and a passage extending therethrough, and wherein the annular shaped member positioned such that the outer wall is disposed adjacent the neck of the aneurysm to substantially seal the aneurysm and the passage is disposed coaxially within the body lumen to allow continued fluid flow along the body lumen.

In addition or alternatively, the tubular member may include a balloon carried on the distal end thereof, and wherein the fluid is delivered via the balloon. For example, the balloon may include one or more openings extending through a wall of the balloon and communicating with an interior of the balloon, the fluid being delivered into the aneurysm through the one or more openings. In one embodiment, the fluid may be introduced into the interior of the balloon, thereby expanding the balloon until the one or more openings expand sufficiently to allow the fluid to exit from the interior of the balloon through the one or more openings. Alternatively, the balloon may include a delivery lumen formed within a wall of the balloon and the fluid may be delivered into the aneurysm through the delivery lumen. In another alternative, the balloon may carry one or more abrasive elements configured for disrupting the endothelium of the wall of the aneurysm, as described above.

In accordance with yet another aspect of the present invention, a method is provided for treating a wall of an aneurysm, blood vessel, or other body lumen. A tubular member may be introduced into the body lumen until a distal end of the tubular member is located adjacent the aneurysm, the distal end carrying an annular shaped member. The annular shaped member may be expanded until an outer wall of the annular shaped member engages a neck of the aneurysm to substantially seal the aneurysm, the annular shaped member including a passage extending-therethrough to allow continued fluid flow along the body lumen. A fluid may be delivered into the aneurysm to at least partially de-endothelialize the wall of the aneurysm, thereby causing an endothelium of the wall to generate fibrous tissue to strengthen the wall of the aneurysm.

In accordance with still another aspect of the present invention, an apparatus is provided for disrupting an endothelium of an aneurysm or other body lumen that includes an outer member including a proximal end and a distal end having a size and shape for insertion into a body lumen communicating with an aneurysm or other body lumen. An inner member may be deployable from within the outer member that includes a proximal end, a distal end having a size and shape for insertion into an aneurysm cavity or body lumen, and a lumen extending between the proximal end and an outlet port on the distal end. A source of de-endothelialization fluid may be coupled to the proximal end of the tubular member and communicating with the first lumen. A sealing member may be carried by one of the inner and outer members proximal to the outlet port, the sealing member having a size and shape for substantially sealing a neck of the aneurysm or other body lumen.

In accordance with yet another aspect of the present invention, a method is provided for treating a malformation extending from a body lumen, such as an arterio-venous malformation or fistula. A tubular member may be introduced into the body lumen until a distal end of the tubular member is located within the malformation. The malformation may be substantially sealed from the body lumen, and fluid aspirated from within the malformation. For example, the malformation may be flushed with fluid, such as saline, and excess fluid may be aspirated from the malformation to substantially clear the malformation. Preferably, the malformation is flushed and aspirated substantially simultaneously.

In one embodiment, the malformation may be substantially sealed form the body lumen by expanding an occlusion member carried on the distal end of the tubular member to engage an entrance into the malformation. In another embodiment, an occlusion member, such as a compliant balloon, may be introduced into the body lumen until the occlusion member is adjacent the malformation and then expanded to engage an entrance to the malformation.

A therapeutic fluid may be delivered via the tubular member into the malformation, e.g., to at least partially de-endothelialize an endothelium of the malformation. In addition or alternatively, the therapeutic fluid may cause at least one of the following to occur within the malformation: cellular lysis, disruption of cellular or intercellular adhesions, and disruption of cellular function. Thereafter, the therapeutic fluid may be aspirated from the malformation, e.g., by simultaneous flushing and aspirating. If one or more occlusion members were used to seal malformation, the occlusion member(s) may be collapsed or otherwise removed from the body lumen, allowing the malformation to communicate with the body lumen.

Where the malformation is an arterio-venous malformation or fistula, e.g., extending between an artery and a vein or two other blood vessels, an occlusion may be introduced into the artery or first vessel to substantially isolate the artery or first vessel from the arterio-venous malformation. Another occlusion member may be introduced into the vein or second vessel to substantially isolate the vein or second vessel from the arterio-venous malformation. Thus, the malformation may be substantially isolated from both vessels, e.g., to allow flushing, aspiration, and/or therapeutic fluid infusion only within the malformation. Where infusion and aspiration are simultaneous, one of the occlusion members may be used for infusion, while the other occlusion member may be used for aspiration.

In accordance with still another aspect of the present invention, an apparatus is provided for disrupting an endothelium of a wall of an aneurysm or other body lumen that includes an elongate core member having an outer surface, a proximal end, and a distal end having a size and shape for introduction into an aneurysm or other body lumen. One or more fibers are provided on the outer surface of the core member, the one or more fibers carrying a de-endothelialization agent.

The apparatus may be used to at least partially de-endothelialize a wall of an aneurysm or other body lumen. The core member may be introduced into the aneurysm or other body lumen, thereby releasing the fluid from the one or more fibers within the aneurysm or other body lumen, the fluid disrupting at least a portion of the endothelium of the wall of the, aneurysm or other body lumen. The core member may be dipped in a source of de-endothelialization fluid such that the one or more fibers absorb the fluid.

Alternatively, the core member may include a coating, e.g., a hydrogel, on the outer surface of the core member that is degradable when exposed to bodily fluid, the coating including a de-endothelialization agent that is released as the degrades.

To at least partially de-endothelialize a wall of an aneurysm or other body lumen, the core member may be introduced into the aneurysm. The core member may be left within the aneurysm or other body lumen until the coating at least degrades to release the de-endothelialization agent within the aneurysm or other body lumen, whereby the agent may at least partially de-endothelialize a wall of the aneurysm or other body lumen.

Other objects and features of the present invention will become apparent from consideration of the following description taken in conjunction with the accompanying drawings.

BRIEF DESCRIPTION OF THE DRAWINGS

The drawings illustrate the design and utility of preferred embodiments of the present invention, in which similar elements are referred to by common reference numerals. In order to better appreciate how the advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings.

FIG. 29A is a partial cross-sectional side view of a de-endothelialization device electrically coupled to a generator.

FIG. 29B is a partial cross-sectional side view of a de-endothelialization device conductively coupled to a heatable element.

FIG. 30 is a cross-sectional side view of a de-endothelialization device including an operative element for delivering heat to an endothelium of an aneurysm.

FIG. 31 is a cross-sectional view of a de-endothelialization fluid delivery device delivering fluid into an aneurysm.

DETAILED DESCRIPTION OF THE PREFERRED EMBODIMENTS

Systems and methods of de-endothelializing an aneurysm or other body lumen are described herein. As used in this specification, "de-endothelializing" or "de-endothelialization" refers to the process of disrupting an endothelium of an aneurysm or other body lumen, which includes removing, damaging physically, damaging normal biochemical function, or otherwise damaging and/or destroying a part or all of the endothelium of the wall of an aneurysm or other body lumen. The first part of the specification discusses systems and methods of de-endothelializing an aneurysm or other body lumen using mechanical instrumentality. The second part of the specification discusses systems and methods of de-endothelializing an aneurysm or other body lumen using a thermal treatment. The third part of the specification discusses systems and methods of de-endothelializing an aneurysm or other body lumen using a fluid.

I. De-Endothelialization Using Mechanical Instrumentality

A. Implantable De-Endothelialization Devices

Figure 1:
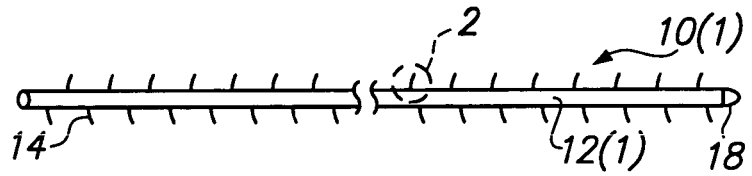
FIG. 1 is a side view of a de-endothelialization device.

FIGS. 1-11 show variations of a de-endothelialization device 10. The de-endothelialization device 10 includes a core member 12 and one or more abrasive elements 14 coupled to the core member 12. In general, the core member 12 carries the abrasive element(s) 14, which are adapted for disrupting an endothelium of an aneurysm. Optionally, the de-endothelialization device 10(1) may include an end cap 18, as shown in FIG. 1, e.g., a rounded and/or substantially blunt distal tip.

FIG. 1 shows a de-endothelialization device 10(1) that has an elongate core member 12(1) adapted to be implanted within an aneurysm. The core member 12(1) preferably has a circular cross-sectional shape. Alternatively, the core member 12(1) may have a rectangular, a triangular, or other geometric cross-sections. The core member 12(1) may even have an irregular shaped cross-section.

The core member 12(1) is preferably made of biodegradable materials. Biodegradable or absorbable materials suitable for use in the compositions of the core member 12(1) may include polymers and proteins. Suitable polymers include, for example, polyglycolic acid, polylactic acid, polycaprolactone, polyhydroxybutyrate, polyhydroxyvalerate, polydioxanone, polycarbonates, polyanhydrides, polyhydroxyalkanoates, polyarylates, polysaccharides, polyamino acids, and copolymers thereof. Non-limiting examples of bioabsorbable proteins include collagen, elastin, fibrinogen, fibronectin, vitronectin, laminin and gelatin. Many of these materials are commercially available. Fibrin-containing compositions are commercially available, for example, from Baxter. Collagen containing compositions are commercially available, for example, from Cohesion Technologies, Inc., Palo Alto, Calif. Fibrinogen-containing compositions are described, for example, in U.S. Pat. Nos. 6,168,788 and 5,290,552, the entirety of which is expressly incorporated by reference herein. As will be readily apparent, absorbable materials can be used alone or in any combination with each other. The absorbable material may be in the form of a monofilament or, alternatively, multi-filament strands.

Furthermore, the absorbable materials may be used in combination with additional components. For example, lubricious materials (e.g., hydrophilic) materials may be used to coat the member. One or more bioactive materials may also be included in the composition of the core member 12(1). The term "bioactive" refers to any agent that exhibits effects in vivo, for example, a thrombotic agent, a therapeutic agent, and the like. Examples of bioactive materials include cytokines; extra-cellular matrix molecules (e.g., collagen); trace metals (e.g., copper); matrix metalloproteinase inhibitors; and other molecules that stabilize thrombus formation or inhibit clot lysis (e.g., proteins or functional fragments of proteins, including but not limited to Factor XIII, $\alpha_2$-antiplasmin, plasminogen activator inhibitor-1 (PAI-1) or the like). Examples of cytokines that may be used alone or in combination in practicing the present invention include basic fibroblast growth factor (bFGF), platelet derived growth factor (pDGF), vascular endothelial growth factor (VEGF), transforming growth factor beta (TGF-β), and the like. Cytokines, extra-cellular matrix molecules, and thrombus stabilizing molecules are commercially available from several vendors such as Genzyme (Framingham, Mass.), Genentech (South San Francisco, Calif.), Amgen (Thousand Oaks, Calif.), R&D Systems, and Immunex (Seattle, Wash.). Additionally, bioactive polypeptides can be synthesized recombinantly as the sequence of many of these molecules are also available, for example, from the GenBank database. Thus, it is intended that the invention include use of DNA or RNA encoding any of the bioactive molecules.

Furthermore, it is intended that molecules having similar biological activity as wild-type or purified cytokines, matrix metalloproteinase inhibitors, extra-cellular matrix molecules, thrombus-stabilizing proteins (e.g., recombinantly produced or mutants thereof), and nucleic acid encoding these molecules may also be used. The amount and concentration of the bioactive materials that may be included in the composition of the core member 12(1) may vary, depending on the specific application, and can be readily determined by one skilled in the art. It will be understood that any combination of materials, concentration, or dosage can be used so long as it is not harmful to the subject.

For the compositions of the core member 12(1), it may also be desirable to include one or more radiopaque materials for use in visualizing the vaso-occlusive members 12(1) in situ. Thus, the vaso-occlusive members 12(1) may be coated or mixed with radiopaque materials such as metals (e.g. tantalum, gold, tungsten or platinum), barium sulfate, bismuth oxide, bismuth subcarbonate, and the like.

Alternatively, the core member 12(1) may be made of non-biodegradable materials, such as metals or alloys, for examples, that are in general more elastic than the biodegradable materials described previously. Suitable metals and alloys for the wire making up the coil include the Platinum Group metals, especially platinum, rhodium, palladium, rhenium, as well as tungsten, gold, silver, tantalum, and alloys of these metals. These metals have significant radiopacity and their alloys may be tailored to accomplish an appropriate blend of flexibility and stiffness. They are also largely biologically inert. Additional coating materials, such as polymer, or biodegradable materials as discussed previously, may be added to the surface of the core member 12(1) to improve the lubricity, healing properties, or thrombogenic properties of the vaso-occlusive device.

The core member 12(1) may also be of any of a wide variety of stainless steels if some sacrifice of radiopacity may be tolerated. Very desirable materials of construction, from a mechanical point of view, are materials that maintain their shape despite being subjected to high stress. Certain "super-elastic alloys" include nickel/titanium alloys, copper/zinc alloys, or nickel/aluminum alloys. Alloys that may be used are also described in U.S. Pat. Nos. 3,174,851, 3,351,463, and 3,753,700, the entirety of which is expressly incorporated by reference herein.

Titanium/nickel alloys known as "nitinol" may also be used in the core member 12(1). These are super-elastic and very sturdy alloys that will tolerate significant flexing without deformation even when used as a very small diameter wire. If nitinol is used in the device, the diameter of the core member 12(1) may be significantly smaller than that of a core member 12(1) that uses the relatively more ductile platinum or platinum/tungsten alloy as the material of construction.

The core member 12(1) may also be made of radiolucent fibers or polymers (or metallic threads coated with radiolucent or radiopaque fibers) such as Dacron (polyester), polyglycolic acid, polylactic acid, fluoropolymers (polytetrafluoroethylene), Nylon (polyamide), or even silk.

Figure 2A:
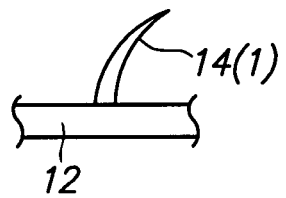
FIG. 2A-2F are details of the de-endothelialization device of FIG. 1, showing various embodiments of an abrasive element.
Figure 2B:
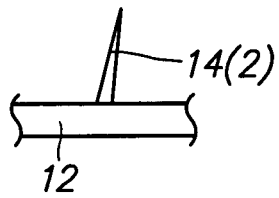
Figure 2C:
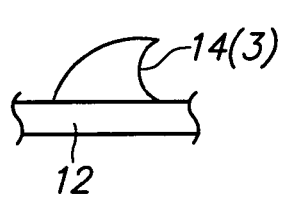
Figure 2D:
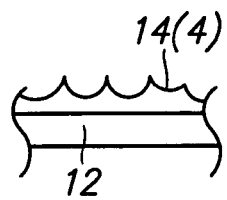
Figure 2E:
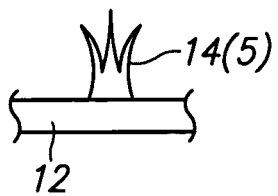
Figure 2F:
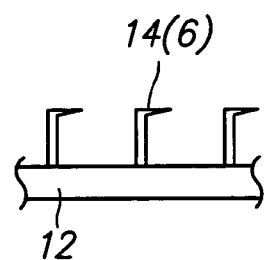

The abrasive element(s) 14 may have a sharp edge (such as that of a cutting wire or a knife) or a sharp point, for the purpose of cutting, abrading, and/or penetrating an endothelium of an aneurysm. FIG. 2 shows several examples of the shape of the abrasive element(s) 14. The abrasive element 14 can have a shape of a hook (FIG. 2A), a needle (FIG. 2B), a fin (FIG. 2C), a saw tooth (FIG. 2D), a multi-branch hook (FIG. 2E), or a ninety degree hook (FIG. 2F). The abrasive element(s) 14 can also include one or more sharp particles, such as diamond dust, that has no specific geometric shape. It should be noted that the abrasive element(s) 14 can also have a customized shape or other shapes as well. The abrasive element(s) 14 can have a wide range of stiffness, so long as the abrasive element(s) 14 is capable of disrupting an endothelium of an aneurysm. Furthermore, in order to prevent over-thinning of the arterial or aneurysm wall, that can risk punctures of the arterial or aneurysm wall, the abrasive element(s) 14 may have an overall depth that is less than about five microns. Depending on the particular application, the abrasive element(s) 14 may also have an overall depth that is more than about five microns.

As a further alternative, the abrasive element 14 may be an abrasive fibrous structure having fibers adapted for disrupting an endothelium of an aneurysm. The fibrous structure is preferably coupled to the core member 12 by frictional contact between the fibrous structure and the outer surface of the core member 12. The surface of the core member 12 may be textured to improve coupling between the fibrous structure and the core member 12. The core member 12 may also include one or more transverse openings along the length of the core member 12, through which strands of the fibrous structure can be wrapped to secure the fibrous structure to the core member 12. Alternatively, the core member 12 may also include protrusions along the length of the core member 12, around which strands of the fibrous structure can be wrapped or hooked to secure the fibrous structure to the core member 12. Alternatively, an adhesive, such as ultraviolet-curable adhesives, silicones, cyanoacrylates, and epoxies, may be used to secure the fibrous structure to the core member 12. Furthermore, the fibrous structure may be coupled to the core member 12 by chemical bonding between reactive groups on the fibrous structure and the core member 12, fusing both materials so that they melt together, or temporarily melting the surface of the core member 12 to embed strands of the fibrous structure.

The abrasive element 14 can be made from a variety of materials, such as polymers, metals, or plastics. Any of the materials discussed previously in reference to the core member 12 may also be suitable for the abrasive element 14. The abrasive element 14 can be coupled to the core member 12 by a polymer, glue, weld, or brazing. Other types of adhesive may also be used, depending on the materials from which the abrasive element 14 and the core member 12 are made. Alternatively, the abrasive element 14 and the core member 12 can be fabricated together as a single unit during a manufacturing process. For example, the abrasive element 14 can be created by removing part(s) of the surface of the core member 12. The abrasive element 14 may also be molded together with the core member 12 when the de-endothelialization device 10 is manufactured. It should be noted that the number of abrasive elements 14, and the patterns or configurations formed by the abrasive elements 14, on the surface of the core member 12 may vary. For example, the de-endothelialization device 10 can have a single or a plurality of abrasive elements 14. Furthermore, the core member 12 can be completely or partially covered by the abrasive element(s) 14 in a random or designed pattern.

The de-endothelialization device 10(1) described above generally has a substantially rectilinear or a curvilinear (slightly curved, i.e. having less than 360° spiral) relaxed configurations. This configuration may be referred to as a "primary shape," i.e., referring to the basic shape of the device material. Such a device may assume folded configurations when they are subjected to an external force, e.g., buckling or compressive forces when they encounter objects.

In addition or alternatively, the vaso-occlusive device may include a "secondary relaxed shape," which may be formed by wrapping a core member having a primary shape that is substantially linear around a shaping element. The secondary shape may be a helical coil or other shapes.

In addition or as a further alternative, the vaso-occlusive device may also assume a "tertiary relaxed shape," which may be formed, for example, by wrapping a core member having a primary or secondary shape around a shaping element. The tertiary shape may be, for example, in a shape of a clover leaf, a twisted figure eight, a flower, a sphere, a vortex, an ovoid, or random shapes.

A secondary and/or tertiary shape may be programmed into a device using known heat treatment processes or other shape memory material properties. Once programmed, the device may be biased to a "relaxed state" including both a primary shape, secondary, and/or tertiary shape. This relaxed state may also be referred to as a lowest energy state, because, when the device is deformed into any other shape, it may store elastic energy that is removed as the device returns towards the relaxed state.

For a device that has a secondary and/or tertiary shape, the core member 12 is preferably made from a substantially resilient material, having sufficient rigidity to support the de-endothelialization device in the secondary and/or tertiary state when deployed, e.g., within an aneurysm or other body space. Thus, the space-filling capacity of these devices may be inherent within the secondary and/or tertiary relaxed shapes of these devices.

Figure 3:
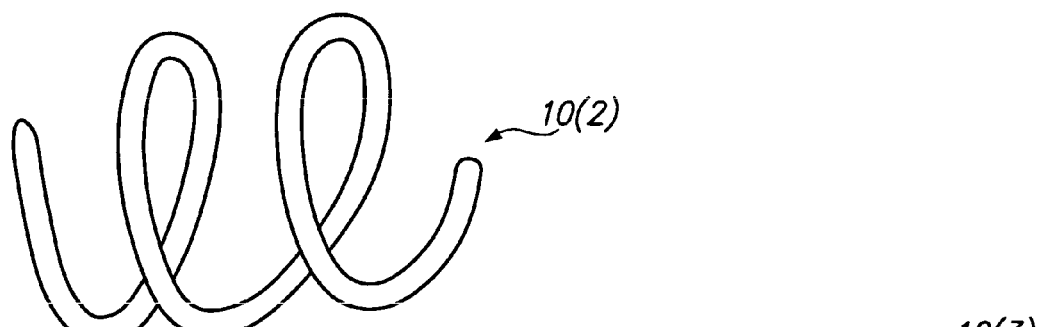
FIGS. 3-11 are exemplary secondary shapes of the de-endothelialization device of FIG. 1.
Figure 4:
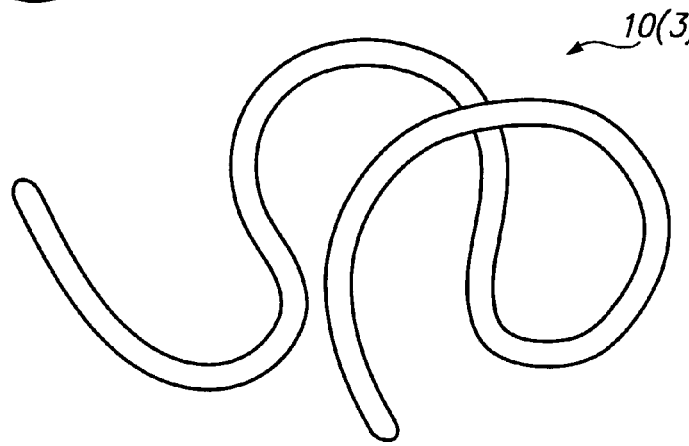

FIGS. 3 and 4 illustrates de-endothelialization devices 10 having secondary shapes. These shapes are simply indicative of the various secondary shapes that may be used, and other shapes may be used as well. The device 10 illustrated in each of the FIGS. 3 and 4 includes the abrasive element 14 as described previously, but is not shown for clarity.

FIG. 3 depicts a de-endothelialization device 10(2) having a secondary shape of a helical coil. The helical coil can have an open pitch, such as that shown in FIG. 3, or a closed pitch. FIG. 4 illustrates a de-endothelialization device 10(3) having a random secondary shape. Each of the secondary shapes shown in FIGS. 3 and 4 may be achieved by wrapping a core member 12 having a primary shape that is substantially linear, such as that shown in FIG. 1, around a mandrel, stylet, or other shaping element. The device 10 may be subjected to a heat treatment or other step known to those skilled in the art for setting the secondary shape of the device 10. Forming devices, such as vaso-occlusive devices, into secondary shapes is well known in the art, and need not be described in further detail.

FIGS. 5-11 illustrate various de-endothelialization devices 10 of this invention having a secondary shape of a helical coil, such as that shown in FIG. 3, and a tertiary shape. These shapes are simply indicative of the various tertiary shapes that may be used, and other shapes may be used as well. While not shown, the devices 10 illustrated in each of the FIGS. 5-11 include the abrasive element 14, as discussed previously.

Figure 5:
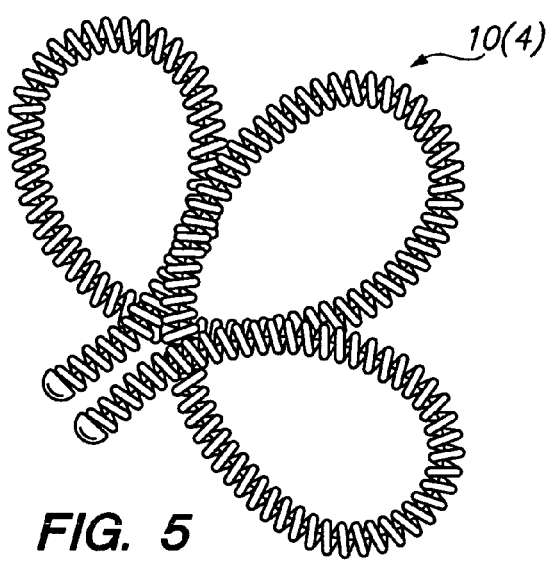
Figure 6:
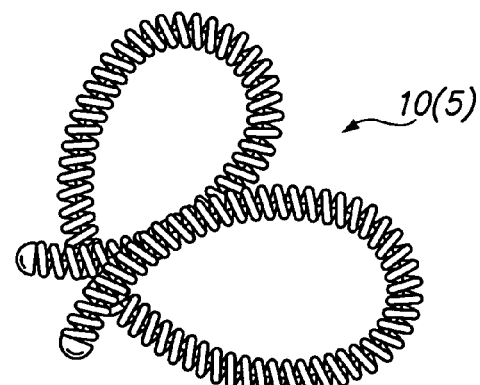
Figure 7:
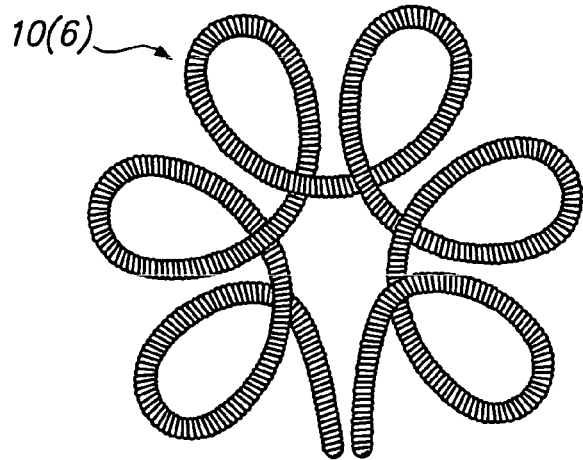
Figure 8:
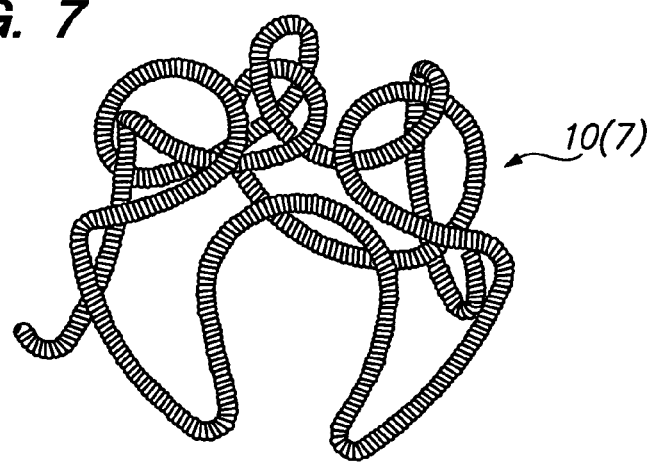
Figure 9:
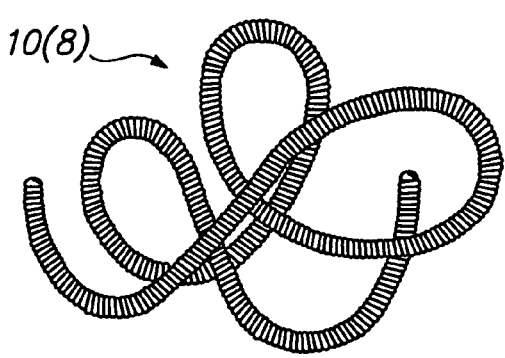
Figure 10:
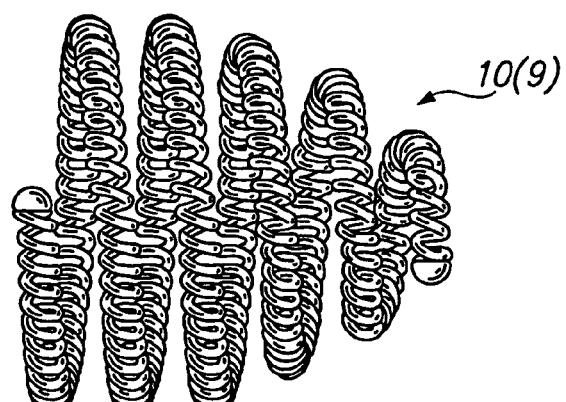
Figure 11:
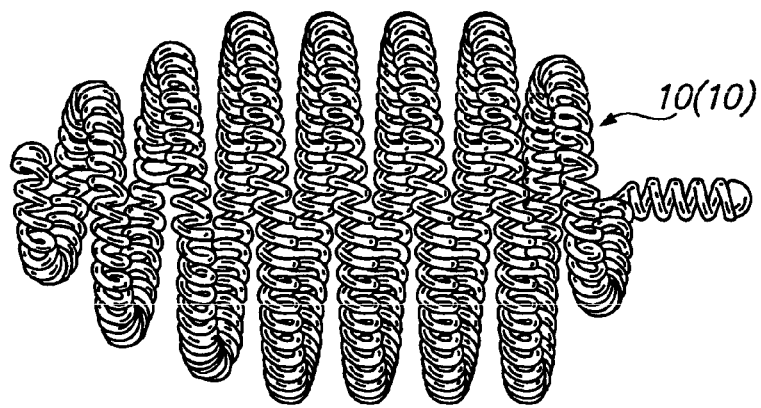
Figure 12:
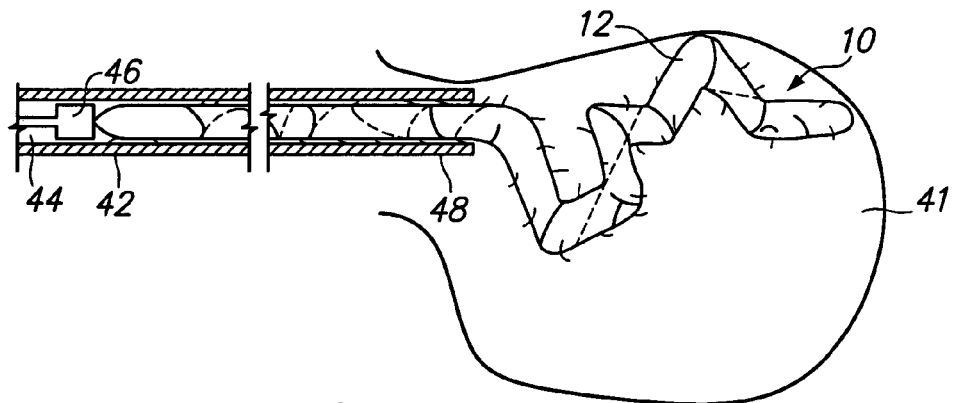
FIG. 12 is a partial cross-sectional side view of a catheter for delivering a de-endothelialization device into an aneurysm.
Figure 13:
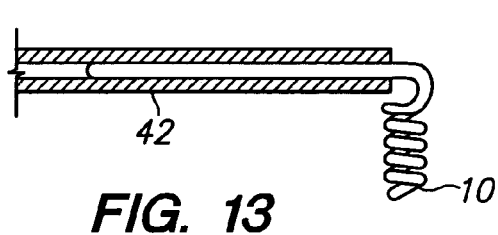
FIG. 13 is a partial cross-sectional side view of a catheter delivering a de-endothelialization device therefrom.

FIG. 5 depicts a device 10(4) having a tertiary shape of a clover leaf. FIG. 6 depicts a device 10(5) having a tertiary shape of a twisted FIG. 8. FIG. 7 depicts a device 10(6) having a flower-shaped tertiary shape. FIG. 8 depicts a device 10(7) having a substantially spherical tertiary shape. FIG. 9 illustrates a device 10(8) having a random tertiary shape. FIG. 10 illustrates a device 10(9) having tertiary shape of a vortex. FIG. 11 illustrates a device 10(10) having a tertiary shape of an ovoid. It should be noted that de-endothelialization device 10 may also have other secondary and tertiary shapes, and should not be limited to the examples illustrated previously. For example, the core member 12, and accordingly, the de-endothelialization device, can be selectively sized to fill a particular aneurysm.

To make the tertiary shaped de-endothelialization devices 10, a core member 12 that is substantially rectilinear or curvilinear may be wrapped around a mandrel or other shaping element to form a secondary shape, such as the helical coil shown in FIG. 3. The mandrel and the core member 12 may be heated to shape the core member 12 into the secondary shape. The secondary shaped core member 12, or as in the case for the devices shown in FIGS. 5-11, the helical coil, is then wrapped around another shaping element to produce the tertiary shape. Heat may also be used to shape the core member 12 to form the tertiary shape. Stable coil designs, and methods of making such, are described in U.S. Pat. No. 6,322,576B1 to Wallace et al., the entirety of which is expressly incorporated by reference herein. It should be noted that forming devices, such as vaso-occlusive devices, into secondary and tertiary shapes is well known in the art, and need not be described in further detail.

The method of using the previously described de-endothelialization devices will now be discussed with reference to FIGS. 12-15. First, a delivery catheter 42 is inserted into the body of a patient, e.g., percutaneously through a peripheral vessel, such as a femoral, carotid, or radial artery. Other entry sites sometimes are well known to physicians who practice these types of medical procedures. The delivery catheter 42, which may be a micro-catheter, sheath, or other elongate device, is positioned so that the distal end 48 of the delivery catheter 42 is appropriately situated, e.g., within the mouth of the body cavity 41 to be treated. The delivery catheter 42 may be advanced over or otherwise in conjunction with a guidewire, guiding catheter, or other rail, as is known in the art. In addition, the catheter 42 may be monitored, e.g., using fluoroscopy, during advancement.

Once the delivery catheter 42 is in place, the de-endothelialization device 10 may be inserted from the proximal end (not shown) of the delivery device 42 into a lumen of the delivery catheter 42. If desired, the de-endothelialization device 10 can be heated, e.g., to a temperature above 50° C., or cooled, e.g., to a temperature below 0° C., to enhance the de-endothelializing property of the de-endothelialization device 10. The endothelium of the aneurysm or other body lumen can be injured or destroyed simply by heating, e.g., to a temperature above 50° C., or cooling, e.g., to a temperature below 0° C., as explained further below.

For a de-endothelialization device, such as the device 10 shown in FIG. 1 having no secondary shape, the de-endothelialization device 10 may naturally assume its substantially rectilinear or a curvilinear primary shape when disposed within the lumen of the delivery catheter 42, without being subjected to substantial stress. When the de-endothelialization device 10 is disposed within the lumen of the delivery catheter 42, the abrasive element(s) 14 may assume a bent or collapsed configuration. Alternatively, the lumen of the delivery catheter 42 can be made sufficiently wide to accommodate the de-endothelialization device 10 without substantially bending the abrasive element(s) 14. For de-endothelialization devices having secondary and/or tertiary shapes, such as the de-endothelialization devices shown in FIGS. 3-11, they may be "stretched" or straightened to a substantially linear shape primary or secondary shape while residing within the lumen of the delivery catheter 42, as illustrated with the de-endothelialization device 10 in FIG. 13. A de-endothelialization device that can assume a linear shape within the delivery device 42 may substantially reduce the cross-sectional dimension required of the delivery catheter 42, which may assist advancing the catheter 42 into the body of a patient and improves the maneuverability of the catheter 42 within the body, e.g., through narrow vessels and/or tortuous anatomy.

Figure 14:
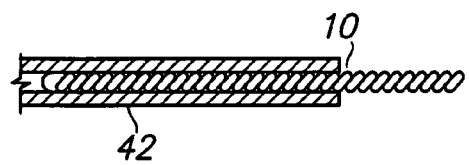
FIG. 14 is a partial cross-sectional side view of a catheter delivering another de-endothelialization device therefrom.
Figure 15:
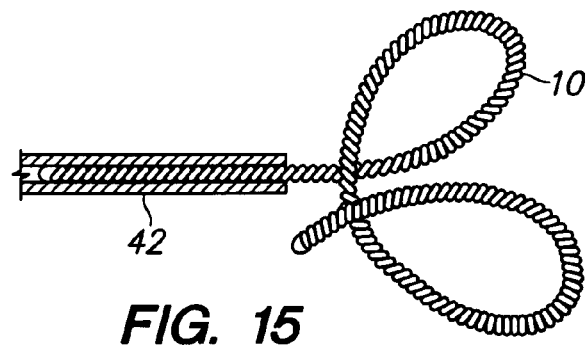
FIG. 15 is a partial cross-sectional side view of a catheter delivering yet another de-endothelialization device therefrom, showing the de-endothelialization device adopting a secondary shape as it is deployed.

Alternatively, as shown in FIG. 14, a de-endothelialization device having a secondary shape of a helical coil, such as the de-endothelialization device 10, may be disposed within the lumen of a delivery catheter in an unstretched configuration. Furthermore, as shown in FIG. 15, a de-endothelialization device having a secondary shape made of a helical coil, such as the de-endothelialization device 10, may be "stretched" from its tertiary shape into a substantially linear helical coil, when disposed within the lumen of a delivery catheter 42.

Referring back to FIG. 12, the de-endothelialization device 10 is preferably advanced distally towards the distal end 48 of the delivery catheter 42 using a core wire or pusher member 44. A plunger 46 may be attached to the distal end of the core wire 44 to assist advancing the de-endothelialization device 10. Alternatively, fluid pressure may also be used to advance the de-endothelialization device 10 along the delivery catheter 42. The inner diameter of the delivery catheter 42 should be made large enough to allow advancement of the de-endothelialization device 10. On the other hand, the inner diameter of the delivery catheter 42 should not be significantly larger than the overall cross-sectional dimension of the de-endothelialization device 10 in order to avoid bending and kinking of the de-endothelialization device 10 within the lumen of the delivery catheter 42.

For a de-endothelialization device having no secondary relaxed shape or having a secondary shape that is substantially rectilinear or curvilinear, such as a substantially linear helical coil, the de-endothelialization device may remain substantially rectilinear or curvilinear without undergoing substantial stress while disposed within the lumen of the delivery catheter 42. Once the de-endothelialization device 10 or a portion of the de-endothelialization device 10 exits from the distal end 48 of the delivery catheter 42, it may remain substantially rectilinear or curvilinear until it contacts an object, e.g., the wall of the body cavity 41. If the de-endothelialization device 10 is advanced further distally, i.e., to introduce additional length into the body cavity, the de-endothelialization device 10 may buckle and/or bend due to the distal force exerted by the device against the object that it contacts. Consequently, the de-endothelialization device 10 may fold, thereby forming a three-dimensional structure for occupying the aneurysm. For de-endothelialization devices having secondary and/or tertiary shapes, the de-endothelialization device may attempt to assume its relaxed secondary and/or tertiary shape when ejected from the lumen of the delivery catheter 42. The shape of the secondary and/or tertiary shapes may help fill the body cavity 41.

Optionally, one or more additional de-endothelialization devices 10 may also be placed within the body cavity 41 by repeating the relevant steps discussed above. When a desired number of de-endothelialization devices have been placed within the body cavity 41, the delivery catheter 42 is then withdrawn from the body cavity 41.

During and/or after placing the de-endothelialization devices 10 in the body cavity 41, the abrasive element(s) 14 of the de-endothelialization device(s) may disrupt the endothelium of the aneurysm, blood vessel, or other body lumen, causing the lumen wall to produce a fibro-proliferative reaction. As a result, fibrous tissue containing collagen may form at the disrupted endothelium, thereby thickening the wall of the aneurysm or body lumen. The thickening of the wall of the aneurysm or body lumen may reduce the risk of rupturing and/or growth of the aneurysm, thereby enhancing stabilization of the aneurysm, and/or enhancing stable occlusion of the aneurysm or body lumen. Eventually, an embolism may form to occlude the body cavity 41.

Figure 16:
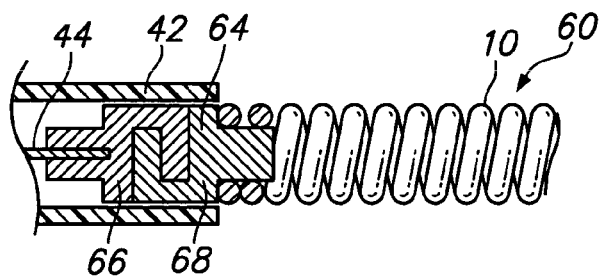
FIG. 16 is a partial cross-sectional detail of a de-endothelialization device coupled to a core wire by a mechanical joint.

FIG. 16 depicts an embodiment, generally designated 60, having a de-endothelialization device 10 that may be detached from a core wire 44 using a mechanical joint 64. The de-endothelialization device 10 may be any one of the devices depicted in FIGS. 1-11 and described above, including one or more abrasive elements 14 (not shown for clarity). Joint 64 has a clasp section 66 that remains attached to the core wire 44 when sheath or catheter body 42 is retracted proximally. Joint 64 also includes a second clasp section 68 that is carried on the proximal end of the de-endothelialization device 10 and interlocks with clasp section 66 when the assembly is within sheath 42. When the sheath 42 is withdrawn from about the assembly, the clasp sections are free to disengage, thus detaching the de-endothelialization device 10. Core wire 44 may be electrically connected to a source of radiofrequency energy.

The de-endothelialization devices 10 described herein may also be non-detachable or detachable by electrolytic joints or connectors, such as those described in U.S. Pat. Nos. 5,234, 437, 5,250,071, 5,261,916, 5,304,195, 5,312,415, and 5,350, 397, the entireties of which are expressly incorporated by reference herein.

Figure 17:
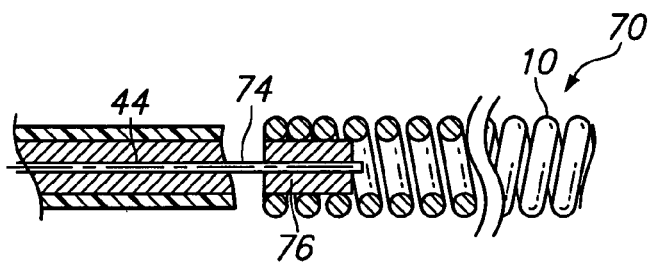
FIG. 17 is a partial cross-sectional detail of a de-endothelialization device coupled to a core wire by an electrolytic link.

FIG. 17 shows an embodiment, generally designated 70, having a de-endothelialization device 10 that may be detached from a core wire 44 using a joint 74 susceptible to electrolysis. The de-endothelialization device 10 may be any one of the devices depicted in FIGS. 1-11 and described above, including one or more abrasive elements 14 (not shown for clarity). Such joints are described in detail in U.S. Pat. No. 5,423,829, the entirety of which is expressly incorporated by reference herein. Joint 74 may be made of a metal that, upon application of a suitable voltage to the core wire 44, may erode in the bloodstream, thereby allowing the de-endothelialization device 10 to detach. The de-endothelialization device 10 may be made of a metal that is more "noble" in the electromotive series than the metal of joint 74. A return electrode (not shown) may be supplied to complete the circuit, as is well know to those skilled in the art. The region of core wire 44 proximal to the joint 74 may be insulated to focus the erosion at the joint 74. An electrically conductive bushing 76 is used to connect the distal end of core wire 44 to the proximal end of the de-endothelialization device 10.

For a de-endothelialization device 10 that is detachably coupled to the core wire 44 (such as those illustrated in FIGS. 16 and 17), the de-endothelialization device 10 may be moved, i.e., advanced, retracted, and/or rotated, within the aneurysm or other body lumen by manipulating (i.e., advancing, retracting, and/or rotating) the proximal end of the core wire 44. Moving the de-endothelialization device 10 within the aneurysm or other body lumen may increase the surface area of the endothelium disrupted by the abrasive element(s) 14 of the de-endothelialization device 10. After the endothelium of the aneurysm or other body lumen has been sufficiently, disrupted, the de-endothelialization device 10 may be de-coupled from the core wire 44. If desired, one or more additional de-endothelialization device(s) 10 may be inserted into the aneurysm or other body lumen, as discussed previously.

Although, the de-endothelialization device 10 described previously is adapted to be implanted in a body cavity, such needs not be the case. After the endothelium of the aneurysm or other body lumen has been disrupted, the de-endothelialization device 10 may be removed from the aneurysm or other body lumen by retracting the proximal end of the core wire 44, thereby causing the de-endothelialization device 10 to move back into the lumen of the catheter body 42. As such, the de-endothelialization device 10 may be used as a tool without being implanted in a body cavity. Thereafter, one or more vaso-occlusive devices may be delivered to fill the aneurysm or other body lumen. If the aneurysm or other body lumen is small, the de-endothelialization of the aneurysm may cause the wall to thicken enough to occlude the aneurysm or other body lumen without using a vaso-occlusive device. De-endothelialization devices not intended for implantation are described further below.

B. Non-Implantable De-Endothelialization Devices

FIGS. 18-24 show variations of a de-endothelialization device 100 that is adapted to be removed from an aneurysm or other body lumen after an endothelium of the aneurysm or other body lumen has been disrupted.

Figure 18:
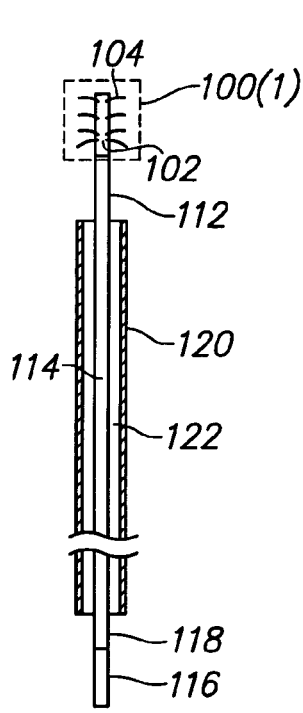
FIG. 18 is a partial cross-sectional side view of a de-endothelialization device coupled to a core member and being deployed from a delivery catheter.
Figure 19:
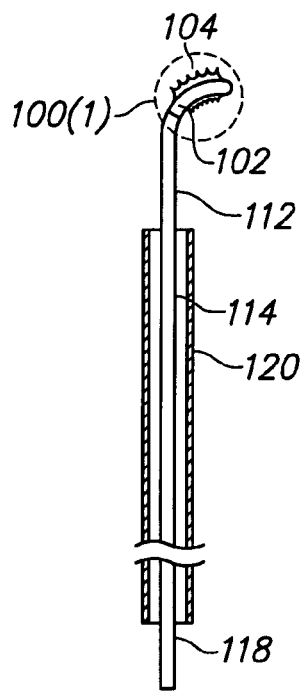
FIG. 19 is a partial cross-sectional side view of an alternative embodiment of the de-endothelialization device of FIG. 18, showing the de-endothelialization device having a curvilinear relaxed shape.
Figure 20:
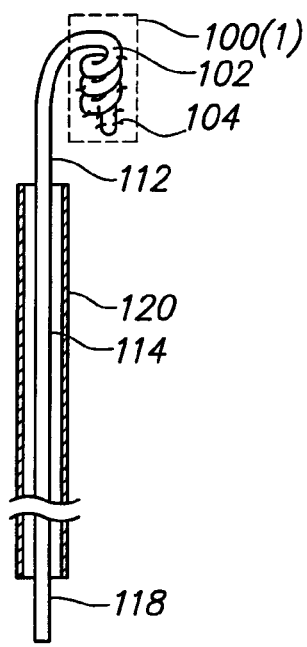
FIG. 20 is a partial cross-sectional side view of another alternative embodiment of the de-endothelialization device of FIG. 18, showing the de-endothelialization device having a relaxed shape of a spiral.

FIG. 18 shows a de-endothelialization device 100(1) having a core member 102 and one or more abrasive elements 104 coupled to the core member 102. The abrasive element(s) 104 may be any of the variations of the abrasive element 14 discussed previously. Any of the materials discussed previously with reference to the core member 12 may also be used to construct the core member 102. The core member 102 is preferably detachably coupled to a distal end 112 of an elongate member, such as a core wire or a pusher member 114. Thus, if the core member 102 becomes irretrievable during a procedure, the core member 102 can be decoupled from the elongate member 114, and left within the aneurysm or other body lumen as an implant. Alternatively, the core member 102 may be secured to the distal end 112 of the elongate member 114 by a suitable adhesive, which may depend upon the materials from which the elongate member 114 and the core member 102 are made. The core member 102 may also be fabricated together with the elongate member 114 as one unit during manufacturing. In this case, the core member 102 would include the elongate member 114. A handle 116 may optionally be secured to a proximal end 118 of the elongate member 114.

The core member 102 and/or the distal end 112 of the elongate member 114 may assume a substantially linear shape, such as that shown in FIG. 18. Alternatively, the core member 102 may also assume a relaxed configuration that has a curvilinear shape, such as a J-shape (FIG. 19), a spiral (FIG. 20), or other designed shapes. In general, any of the shapes-discussed previously with reference to FIGS. 1-11 may also be used for the core member 102. Although not required, the de-endothelialization device 100(1) may optionally include a tubular element 120 (such as a sheath or a catheter) capable of coaxially surrounding the core member 102 during a procedure. The core member 102 and/or the distal end 112 of the elongate member 114 assumes a low profile configuration when disposed within a lumen 122 of the tubular element 120. If the core member 102 and/or the distal end 112 of the elongate member 114 has a non-linear relaxed configuration, the core member 102 and/or the distal end 102 may assume its relaxed configuration when deployed from the tubular element 120.

Figure 21A:
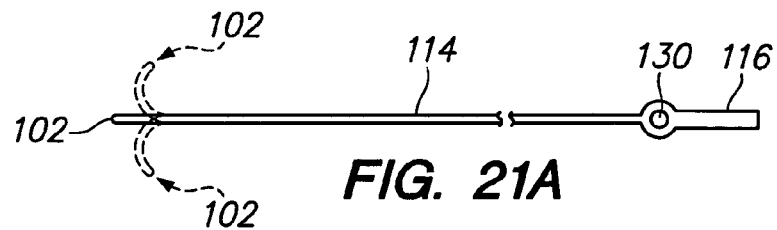
FIG. 21A is a top view of an embodiment of a de-endothelialization device including a steering mechanism.
Figure 21B:
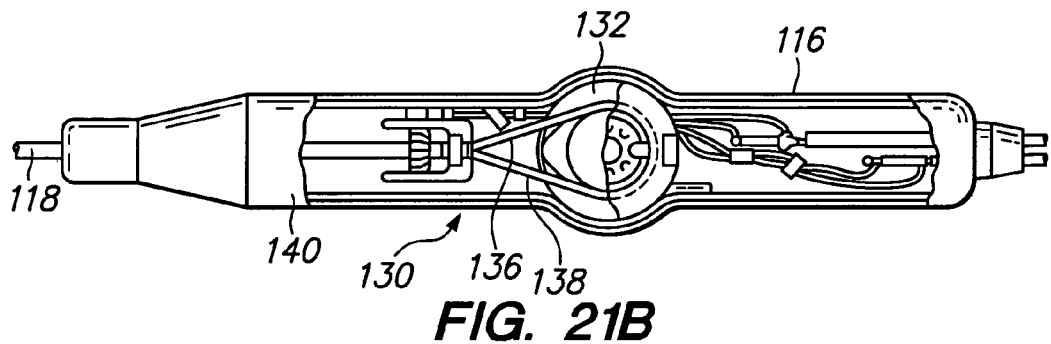
FIG. 21B is a partial cross-sectional top view of the de-endothelialization device of FIG. 21A expanded after being deployed from the catheter.

Turning to FIG. 21A, optionally, the de-endothelialization device 100 may include a steering mechanism 130 for changing the shape of the distal end 112 of the elongate member 104. The steering mechanism 130 can vary. For example, FIG. 21 shows a steering mechanism as disclosed in U.S. application Ser. No. 07/789,260, now U.S. Pat. No. 5,363,861 issued Nov. 15, 1994, the entirety of which is expressly incorporated by reference herein. As FIG. 21B shows, the steering mechanism 130 may include a rotating cam wheel 132 within the handle 116, and an external steering lever or control (not shown) may rotate the cam wheel 132. The cam wheel 132 holds the proximal ends of right and left steering wires 136 and 138. The steering wires 136 and 138 may extend along the associated left and right side surfaces of the cam wheel 132 and through the guide tube 140. The steering wires 136 and 138 connect to left and right sides of a resilient bendable wire or spring within a distal section of the elongate member 104. Alternatively, the steering wires 136 and 138 may connect to a portion of the core member 102.

As FIG. 21A shows, manipulating the steering lever or control causes the distal end 112 of the elongate member 104 and/or the core member 102 to bend up or down. By rotating the handle, thereby bending the distal end 112 of the elongate member 104, and by manipulating the steering lever, it is possible to maneuver the distal end 112 of the elongate member 104 virtually in any direction. The steerable section simplifies the positioning of the distal end 102, and accordingly, the core member 102 of the de-endothelialization device 100.

When using the de-endothelialization device 100, the distal end 112 (including the de-endothelialization device 100) of the elongate member 104 is first positioned inside an aneurysm or other body lumen. Positioning the distal end 112 of the elongate member 104 may be facilitated using a guide wire and/or sheath (such as the tubular element 120), as is known to those skilled in the art. If desired, the de-endothelialization device 100 may be heated or cooled to a certain temperature to enhance the de-endothelializing capability of the de-endothelialization device 100, as discussed previously. Next, by manipulating (i.e., advancing, retracting, and/or turning) the proximal end 118 of the elongate member 104 (or the handle 116 if one is provided), the core member 102 of the de-endothelialization device 100 may be positioned at various locations against the endothelium of the aneurysm or other body lumen, thereby disrupting the endothelium of the various locations of the aneurysm or other body lumen. If a steering mechanism 130 is provided, the steering mechanism 130 may also be used to position the core member 102 of the de-endothelialization device 100.

After the abrasive element 104 of the de-endothelialization device 100 has disrupted sufficient surface area of the endothelium of the aneurysm or other body lumen, the de-endothelialization device 100 may be withdrawn from the aneurysm or other body lumen. After some time, fibrous tissue may form at the disrupted endothelium, causing the wall of the aneurysm or other body lumen to thicken, as discussed above with reference to implantable de-endothelialization devices. For an aneurysm or other body lumen having a certain size, it may be desirable to deliver one or more vaso-occlusive device(s) into the aneurysm or other body lumen after the de-endothelialization device 100 has been removed from the aneurysm or other body lumen. Alternatively, if the aneurysm or other body lumen is small, the de-endothelialization of the aneurysm or other body lumen may cause the wall to thicken enough to occlude the aneurysm or other body lumen without requiring a vaso-occlusive device to be implanted.

In certain situations, it may be desirable to disrupt the neck of an aneurysm, with or without de-endothelializing the wall of the aneurysm sac. For example, when the neck of an aneurysm is small, de-endothelializing just the neck may cause the neck of the aneurysm to thicken, thereby closing the neck. For a wide neck aneurysm, de-endothelializing the neck of the aneurysm may have the benefit of reducing the size of the neck. It should be noted that the embodiments of de-endothelialization devices described above may also be suitable for disrupting the neck of an aneurysm, and that the methods described above may be used for this purpose.

Figure 22A:
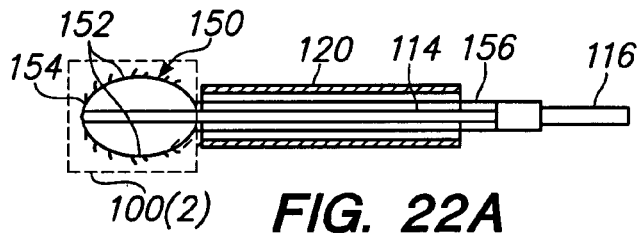
FIG. 22A is a side view of a de-endothelialization device including a basket and being deployed from a delivery catheter.
Figure 22B:
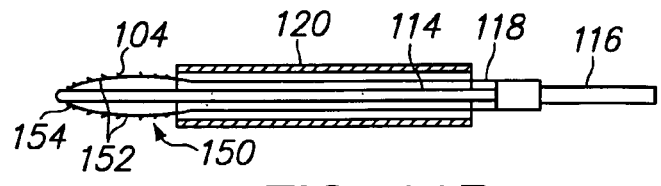
FIG. 22B is a partial side view of the de-endothelialization device of FIG. 22A expanded after being deployed from the catheter.
Figure 23:
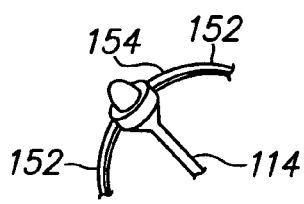
FIG. 23 is a detail of a variation of the de-endothelialization device of FIG. 22A, showing the basket rotatably coupled to a core wire.
Figure 24:
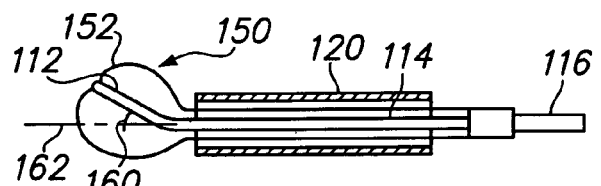
FIG. 24 is a side view of an alternative embodiment of the de-endothelialization device of FIG. 22A, showing a distal end of the core wire biased to define an angle with an axis of a proximal portion of the core wire.

FIGS. 22-24 show variations of a de-endothelialization device 100, including an expandable member coupled to a core wire or other elongate member 114. FIG. 22A shows a de-endothelialization device 100(2) including one or more abrasive elements 104, and an expandable basket 150. Although the expandable basket 150 is shown to include two flexible wires 152, it may include any number of wires 152. Furthermore, the basket 150 is not necessarily limited to the example illustrated in FIG. 22. Alternatively, the basket 150 may include a braided structure or a mesh. The basket 150 is preferably made of an elastic material, such as nitinol, although other materials may also be used. The distal end of the basket 150 may be secured to the elongate member 114 such that rotating the proximal end 118 of the elongate member 114 may cause the expandable basket 150 to rotate. Alternatively, as shown in FIG. 23, the distal end of the expandable basket 150 may be rotatably secured to the elongate member 114 so that the basket 150 can rotate about the elongate member 114. In either case, the basket 150 may be rotated manually or automatically, e.g., by a machine.

As shown in FIGS. 22A and 22B, the basket 150 may assume a low or collapsed profile while disposed within the lumen of the tubular element 120, and is free to assume an expanded profile when it is outside the tubular element 120. The basket 150 may be self-expanding or self-collapsing. A self-expanding basket has a relaxed expanded configuration, and may be collapsed by directing opposite ends 154 and 156 of the wires 152 (or the elements defining the basket 150) further from one another. A self-collapsing basket has a relaxed collapsed (or unexpanded) configuration, and may be expanded by directing opposite ends 154 and 156 of the wires 152 (or the elements defining the basket 150) closer towards one another. The shape of the basket 150 may be changed, for example, by varying the tension or compression on any or all of the wires 152 via a control (not shown). FIGS. 22A and 22B show that the elongate member 114 is substantially linear. Alternatively, as shown in FIG. 24, the distal end 112 of the elongate member 114 may be bent or preformed such that it forms an angle 160 with an axis 162 of a proximal portion of the elongate member 114. Expandable baskets that may be used are described in U.S. Pat. Nos. 5,893,847, 5,925,038, and 6,216,044, the disclosures of which are expressly incorporated by reference herein.

Figure 25A:
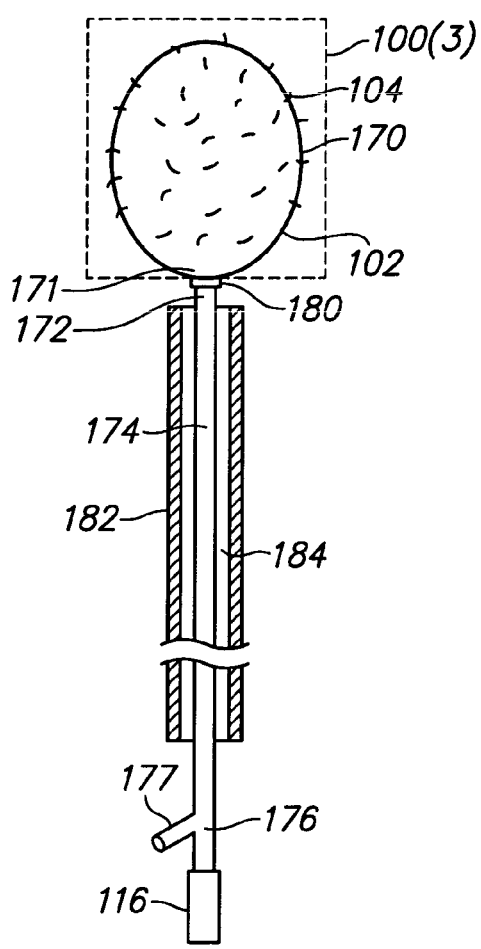
FIG. 25A is a partial cross-sectional side view of a de-endothelialization device including a balloon and coupled to a core wire.

FIG. 25A shows a de-endothelialization device 100(3) that includes a plurality of abrasive elements 104 carried by a balloon 170. The balloon 170 has a proximal end 171 coupled to a distal end 172 of a core tube 174. The core tube 174 also includes a proximal end 176, an opening 177 at the proximal end 176, and a lumen 178 (not shown) extending between the distal end 172 and the proximal end 176.

The proximal end 171 of the balloon 170 is preferably detachably coupled to the distal end 172 of the core tube 174 by a joint 180, such as an electrolytic joint or a mechanical joint, as discussed previously with reference to FIGS. 16 and 17. This may allow the balloon 170 to be de-coupled from the core tube 174 if the balloon 170 cannot be retrieved during a procedure. The balloon 170 may also be secured to the distal end 172 of the core tube 174 by a glue or other suitable adhesive. Alternatively, the balloon 170 can be fabricated with the core tube 174 as one unit during manufacturing. Optionally, the de-endothelialization device 100(3) may include the core tube 174. The endothelialization device 100(3) may also optionally include a tubular element 182, such as a sheath or a catheter, that is capable of surrounding the core tube 174 and the balloon 170 when it is un-inflated.

The balloon 170 is preferably made of thermoplastic or elastomeric materials, such as polyimide (kapton), polyester, silicone rubber, nylon, mylar, polyethylene, or polyvinyl chloride. However, other elastic or inelastic materials known in the art may also be used for constructing the balloon 170. Expandable balloons have been described in U.S. Pat. No. 5,925,083, the entirety of which is expressly incorporated by reference herein.

Figure 25B:
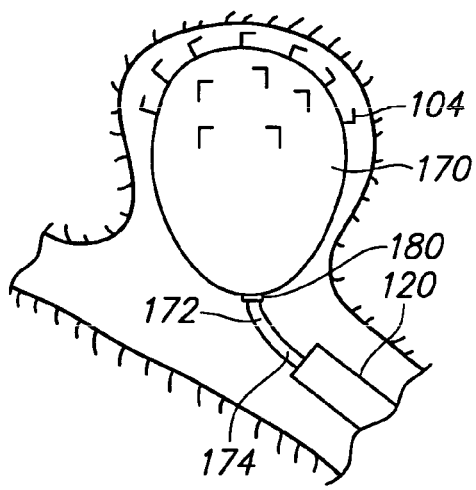
FIG. 25B is a partial cross-sectional side view of a variation of the de-endothelialization device of FIG. 25A, showing abrasive elements forming a pattern at the distal end of the balloon.

It should be noted that the shape of the expandable member (i.e., the basket 150 or the balloon 170) is not necessarily limited to those illustrated in the figures, and other shapes may also be used. Furthermore, various patterns may be formed by the abrasive element(s) 104 on the surface of the expandable member so that only a desired portion of the endothelium of the aneurysm or other body lumen is disrupted. FIG. 25B shows a balloon 170 wherein only the distal end of the balloon 170 is covered by the abrasive elements 104. Other patterns of the abrasive element(s) 104 may also be used.

When using a de-endothelialization device 100 having an expandable member (i.e., the basket 150 or the balloon 170), the tubular element 182 is first positioned so that the distal end of the tubular element 182 is adjacent to a neck of an aneurysm or at the site of another body lumen to be de-endothelialized. The tubular element 182 may be placed using a guide wire or other rail, as is known in the art. The expandable member is initially collapsed and placed within the lumen of the tubular element 182. The expandable member may be inserted into a lumen 184 of the tubular element 182 after the distal end of the tubular element 182 has been placed adjacent to the neck of the aneurysm or at the site of another body lumen to be de-endothelialized. Alternatively, the expandable member may be inserted into the lumen 184 of the tubular element 182 first, and the tubular element 182 carrying the expandable member may then be placed into a vessel leading to the aneurysm or at the site of another body lumen to be de-endothelialized.

The distal tip of the tubular element 182 is preferably placed within the aneurysm or at the site of another body lumen to be de-endothelialized. However, the distal tip of the tubular element 182 may also be placed outside the aneurysm adjacent to the neck of the aneurysm so long as the expandable member can be deployed into the aneurysm, or placed adjacent to the segment of vessel to be de-endothelialized so long as the expandable member can be deployed into the segment of vessel to be de-endothelialized. When the distal tip of the tubular element 182 is positioned as desired, the expandable member is then expanded. For the de-endothelialization device 100 including the balloon 170, the balloon 170 is expanded by delivering a fluid through the opening 177 and into the lumen 178 of the core tube 174. The core tube 174 delivers the fluid into an interior of the balloon 170, thereby expanding the balloon 170. The fluid can be a gas or a liquid, such as water, saline, or blood. A radio-opaque marker (not shown) may be carried at the distal end of the tubular element 182 and/or the expandable member to help positioning the tubular element 182 and/or the expandable member relative to the aneurysm or other body lumen.

If the expandable member has an expanded shape that substantially occupies an aneurysm or other body lumen, the abrasive elements 104 may disrupt the endothelium of the aneurysm or other body lumen when the expandable member is expanded. The expandable member may also have an expanded shape that is slightly larger than the aneurysm or other body lumen to enhance the de-endothelialization property of the de-endothelialization device 100. After the endothelium of the aneurysm or other body lumen is disrupted, the expandable member is then collapsed and removed from the aneurysm or other body lumen.

Alternatively, before the expandable member is collapsed, the expandable member may be moved within the aneurysm or other body lumen by manipulating the handle 116, thereby causing further disruption to the endothelium of the aneurysm or other body lumen. After the abrasive element 104 of the de-endothelialization device 100 has disrupted a sufficient area of the endothelium of the aneurysm or other body lumen, the de-endothelialization device 100 may then be withdrawn from the aneurysm or other body lumen.

II. De-Endothelialization Using Thermal Treatment

A. De-Endothelialization Using a Heated or Cooled Implant

Figure 26:
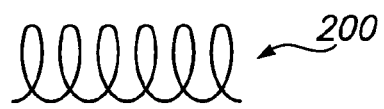
FIG. 26 is a side view of a de-endothelialization device.

The endothelium of an aneurysm can also be disrupted by altering the temperature of the endothelium. As mentioned previously, the endothelium of an aneurysm or other body lumen can be injured or destroyed at a temperature that is above 50° C. or below 0° C. FIG. 26 shows an example of a de-endothelialization device 200 adapted to be heated or cooled to a de-endothelializing temperature. The de-endothelialization device 200 can be a variety of objects, such as a vaso-occlusive device, so long as it is capable of reaching a temperature that is sufficient for disrupting an endothelium of an aneurysm or other body lumen. The de-endothelialization device 200 can be thermally treated by placing it in a freezer or in an oven. Alternatively, the de-endothelialization device 200 can also be thermally treated by placing it in a media, such as water or saline, that has been heated or cooled. Other methods known in the art for altering a temperature of an object can also be used.

The de-endothelialization device 200 can have a variety of shapes or forms. The de-endothelialization device 200 preferably has a relaxed, secondary shape of a helical coil, as shown in FIG. 26. However, any of the shapes discussed previously with reference to FIGS. 1-11 is also applicable to the de-endothelialization device 200. In particular, the de-endothelialization device 200 can have a tertiary shape. The de-endothelialization device 200 can also include an expandable member, such as a balloon or a basket, as discussed previously. Other shapes of devices capable of being placed within a body cavity may also be used, as are known in the art.

The de-endothelialization device 200 should be made from a material that can maintain its structural integrity in a de-endothelializing temperature. That is, the de-endothelialization device 200 should be made from a material such that it will not melt or become too brittle when subjected to the desired thermal treatment. In general, because of their high thermal conductivity, metals are preferable materials for constructing the de-endothelialization device 200. Also, any of the materials discussed previously with reference to the core member 12 of the de-endothelialization device 10 can also be used, so long as the de-endothelialization device 200 remains deliverable to an aneurysm after thermal treatment. Other materials known in the art may also be used for the constructing the de-endothelialization device 200.

Figure 27:
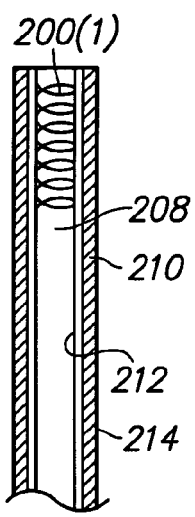
FIGS. 27 and 28 are partial cross-sectional side views of a de-endothelialization delivery device, including a de-endothelialization device having a helical coil shape when disposed and deployed from the delivery device.

FIG. 27 shows a de-endothelialization device 200(1) that is adapted to be thermally treated before it is delivered to an aneurysm or other body lumen. A tubular element 210, such as a sheath or a catheter, is used to deliver the vaso-occlusive device 200(1) to an aneurysm or other body lumen. The tubular element 210 includes an insulative layer 212 at an interior surface of the tubular element 210. The insulative layer 212 prevents or reduces the amount of thermal transfer from the de-endothelialization device 200(1) to an exterior surface 214 of the tubular element 210. The insulative layer 212 is preferably made of a polymer. However, other materials having desired thermal insulation properties known in the art may also be used. If the tubular element 210 is made from a material that possesses desired thermal insulation properties, then the insulative layer 212 becomes optional, and is not required.

Figure 28:
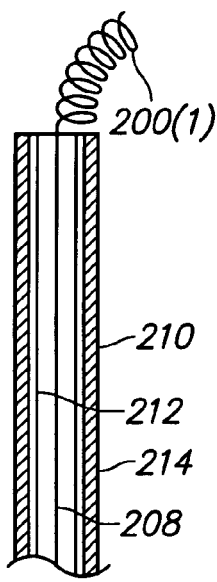

FIG. 27 shows that the de-endothelialization device 200 has a secondary shape of a helical coil when disposed within the lumen of the tubular element 210. However, as discussed previously, such needs not to be the case. As shown in FIG. 28, the de-endothelialization device 200(1) can also be stretched to a substantially linear or curvilinear shape when disposed within the lumen of the tubular element 210. The method of delivering the de-endothelialization device 200(1) is similar to that discussed previously with reference to FIGS. 12-15.

FIG. 29A shows a de-endothelialization device 200(2) that is adapted to be heated after it has been placed within an aneurysm or other body lumen. The de-endothelialization device 200(2) may optionally include a tubular element 224, such as a sheath or a catheter. The de-endothelialization device 200(2) is electrically coupled to a core wire 220 that delivers electrical energy from a source of electrical energy, such as a radio frequency (RF) generator 222, to the device 200(2). The de-endothelialization device 200(2) acts as a resistor and converts the electrical energy to heat. Alternatively, as shown in FIG. 29B, the de-endothelialization device 200(2) may be mechanically coupled to a heatable element 223. The heatable element 223 may act as a resistor and convert electrical energy from the generator 222 to heat. Because of the mechanical coupling between the heatable element 223 and the de-endothelialization device 200(2), heat flows from the heatable element 223 to the de-endothelialization device 200(2) by conduction.

When using the de-endothelialization device 200(2), the de-endothelialization device 200(2) is first placed within the aneurysm or other body lumen by any conventionally known method. For example, the tubular element 224 may first be inserted into a vasculature of a patient such that the distal end of the tubular element 224 is adjacent to an aneurysm or other body lumen. The de-endothelialization device 200(2) can then be delivered to the aneurysm or other body lumen via the tubular element 224.

Once positioned within the aneurysm or other body lumen, the de-endothelialization device 200(2) is then heated. When the temperature of the de-endothelialization device 200(2) reaches a desired level, the de-endothelialization device 200(2) can then be de-coupled from the core wire 220 by methods that are described previously. The tubular element 224 and/or the core wire 220 may optionally include a sensor, such as a thermistor, to monitor the temperature at the distal end of the core wire 220.

Although the de-endothelialization device 200(2) is adapted to be deployed within a body cavity as an implant, such needs not be the case. After the endothelium of the aneurysm or other body lumen has been sufficiently disrupted by the heated de-endothelialization device 200(2), the de-endothelialization device 200(2) can be removed from the aneurysm or other body lumen by retracting a proximal end of the core wire 220, thereby causing the de-endothelialization device 200(2) to retract back into the lumen of a tubular element 224. As such, the de-endothelialization device 200(2) may also be used as a tool without being implanted in a body cavity. One or more vaso-occlusive devices may then be delivered to fill the aneurysm or other body lumen. If the aneurysm or other body lumen is small, the de-endothelialization of the aneurysm may cause the wall to be thicken enough to occlude the aneurysm without using a vaso-occlusive device.

B. De-Endothelialization Using a Heat Delivery Device

FIG. 30 shows a de-endothelialization device 300 that is adapted to deliver heat energy to an endothelium of an aneurysm. The de-endothelialization device 300 includes an operative element 302 and an elongate member 304 having a distal end 306 and a proximal end 308. The operative element 302 is carried at the distal end 306 of the elongate member 304, and is adapted to be electrically coupled to a generator 310. Optionally, the de-endothelialization device 300 may include a sheath 312 having a lumen 314 within which the distal end 306 of the member 304 may slide. Optionally, the de-endothelialization device 300 may also include a steering mechanism, such as that shown in FIGS. 21A and 21B and described above, to facilitate positioning the operative element 302.

The operative element 302 may have a variety of shapes. In general, any of the shapes discussed previously with reference to the de-endothelialization devices 10 shown in FIGS. 1-11 may be used for the operative element 302. The operative element 302 may also include an expandable basket such as that shown in FIGS. 22-24, in which case each of the wires 152 (or the elements making up the basket) may be selectively heated. Alternatively, the operative element 302 may include a balloon, such as that shown in FIG. 25A, in which case the balloon may be heated by supplying and/or circulating heated fluid within the balloon. Cooled fluid may also be used if it is desirable to disrupt the endothelium of an aneurysm or other body lumen using balloon that is below a certain temperature.

When using the de-endothelialization device 300, the operative element 302 is first inserted into a vein or an artery and positioned within an aneurysm or other body lumen. The sheath 312 and/or a guide wire may be used to facilitate positioning the operative element 302, as is known in the art. The de-endothelialization device 300 may optionally include a radio-opaque marker on a distal portion of the member 304 and/or the sheath 312, so that the position of the device can be monitored during the procedure. The operative element 302 may receive electrical energy from the generator 310, and convert the electrical energy generated by the generator 310 to heat.

The operative element 302 may be used to deliver heat to the endothelium of an aneurysm or other body lumen by convection or conduction. Delivering heat to the endothelium by convection does not require the operative element 302 to directly contact the endothelium of the aneurysm or other body lumen. Rather, heat is transferred from the operative element 302 to the endothelium by the medium, such as blood, that is between the operative element 302 and the endothelium. On the other hand, delivering heat to the endothelium by conduction may require the operative element 302 to contact the endothelium of the aneurysm or other body lumen. In either case, the amount of heat generated by the operative element 302 should be sufficient such that the endothelium of the aneurysm or other body lumen is disrupted. The distal end of the elongate member 304 may optionally include a sensor, such as a thermistor, to detect a temperature of the operative element 302. After the de-endothelialization process, the operative element 302 of the de-endothelialization device 300 is then removed from the aneurysm or other body lumen.

C. De-Endothelialization Using a Heat Producing or Cooling Chemical

The endothelium of an aneurysm or other body lumen may also be disrupted by a heat producing chemical. For example, a dual lumen catheter may be used to deliver two fluids, such as calcium chloride and water, that, when mixed, undergo a chemical reaction that produces heat. Alternatively, fluids such as ammonium nitrate and water, known to cause a cooling reaction when mixed may also be used. U.S. patent application Ser. No. 10/150,456, the disclosure of which is expressly incorporated by reference herein, describes a dual lumen catheter that may be suitable for delivering the two heat producing fluids. Other commercially available dual lumen catheters may also be used. Alternatively, a single lumen catheter may be used to deliver the two fluids, sequentially or alternately, to an aneurysm or other body lumen.

III. De-Endothelialization Using a Fluid

A. Delivery of De-Endothelialization Fluid Using a Fluid Delivery Device

The endothelium of an aneurysm or other body lumen may also be disrupted using a fluid 350 that is delivered to the endothelium of the aneurysm. As used herein, "fluid" refers to both liquid and gas. The fluid 350 may be a heated or cooled liquid, such as water or saline. The fluid 350 may also contain any cytotoxic agent including, but not limited to oxidized LDL, perforins, toxin-conjugated antibodies to the endothelial cells, antibodies to the complement protective proteins decay accelerating factor (DAF) (also known as CD55), homologous restriction factor (also known as CD59), membrane cofactor protein (MCP) (also known as CD46), mitochondrial inhibitors, inhibitors of cell membrane ion-pumps, hypotonic fluid, hypertonic solution, CD4 T cells, and/or agents that induce apoptosis/Fas receptor agonists. Enzymes, such as tryspin or collagenase, that are capable of chemically removing the endothelial cells from its basement membranes can also be used. The fluid 350 can also be other drugs, medications, solutions, that are known in the art for disrupting cells or tissues.

FIG. 31 shows a de-endothelialization fluid delivery device 360(1) that includes a delivery tube 362 having a distal end 364, a proximal end 366, and a lumen 368 extending between the distal end 364 and the proximal end 366. The delivery tube 362 may be a catheter, micro catheter, or sheath capable of being inserted into a vasculature of a mammal. The distal end 364 of the delivery tube 362 is adapted to be placed adjacent or within an aneurysm or other body lumen, while the proximal end 366 of the delivery tube 362 is adapted to be coupled to a fluid source 370. The de-endothelialization fluid delivery device 360 may optionally include the fluid source 370. The fluid source 370, which includes a container such as a syringe, a bag, a bottle, or any fluid-holding device, contains the fluid 350 that is capable of disrupting an endothelium of an aneurysm or other body lumen, as discussed previously.

When using the de-endothelialization fluid delivery device 360, the distal end 364 of the delivery tube 362 is first placed within the aneurysm or other body lumen. The distal end of the delivery tube 362 may optionally include a radio-opaque marker to assist positioning the delivery tube 362. When the delivery tube 362 is positioned as desired, the fluid 350 is then delivered from the fluid source 370 to within the aneurysm or other body lumen. Optionally, the fluid source 370 may include a pump or syringe for pressurizing the fluid 350 during the procedure. After the fluid 350 contacts the endothelium of the aneurysm or other body lumen, the de-endothelialization property of the fluid 350 causes the endothelium of the aneurysm or other body lumen to be disrupted. When a desired amount of the fluid 350 has been delivered, the distal end 364 of the delivery tube 362 is then withdrawn from the aneurysm or other body lumen.

Figure 32:
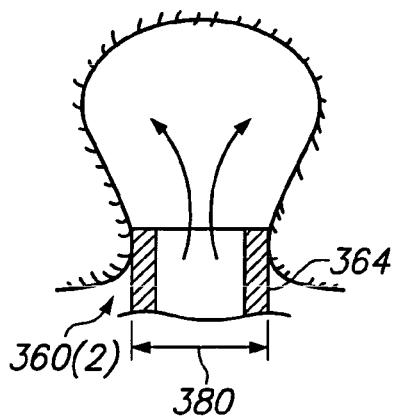
FIG. 32 is a cross-sectional detail of a variation of the de-endothelialization fluid delivery device of FIG. 31.

In certain situations, it may be desirable to prevent the fluid 350 from leaving the aneurysm or other body lumen once the fluid 350 has been delivered into the aneurysm or other body lumen. FIG. 32 shows a de-endothelialization fluid delivery device 360(2) wherein the distal end 364 of the delivery tube 362 has a diameter 380 that is substantially the same or slightly larger than a diameter of an aneurysm or other body lumen. In this case, after the fluid 350 has been delivered to the aneurysm, most or all of the excess fluid 350 may flow back into the lumen 368 of the delivery tube 362. Optionally, a source of vacuum (not shown) may be coupled to the lumen 368 to aspirate fluid from the aneurysm or other body lumen.

Figure 33A:
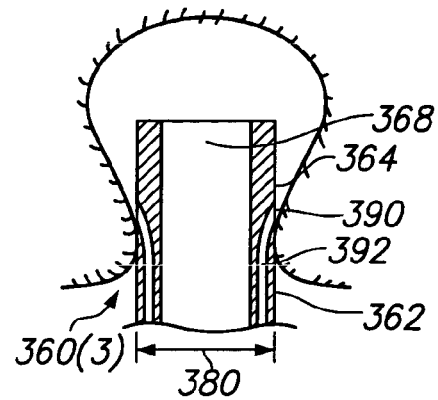
FIG. 33A is a cross-sectional detail of another variation of the de-endothelialization fluid delivery device of FIG. 31 including a drainage port.
Figure 33B:
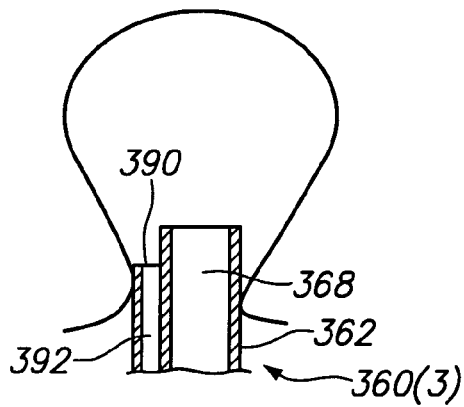
FIG. 33B is a cross-sectional detail of a variation of the de-endothelialization fluid delivery device of FIG. 33A.

FIG. 33A shows another de-endothelialization fluid delivery device 360(3) that includes one or more drainage ports 390 at the distal end 364 of the delivery tube 362. The delivery tube 362 further includes a drainage lumen 392 that is in fluid communication with the drainage port(s) 390. The de-endothelialization fluid delivery device 360(3) also has a distal end diameter 380 that is substantially the same or slightly larger than a diameter of an aneurysm. The drainage ports 390 are located proximal to the distal tip of the delivery tube 362. FIG. 33B shows a variation of the construction of the delivery tube 362 in which the drainage port 390 is also proximal to the distal tip of the delivery tube 362.

When using the de-endothelialization device 360(3), the distal end 364 of the delivery tube 362 is inserted into an aneurysm such that the drainage port(s) 390 is in fluid communication with an interior of the aneurysm. After the fluid 350 has been delivered to the aneurysm through the lumen 368 of the delivery tube 362, most or all of the excess fluid 350 may flow back into the drainage lumen 392 of the delivery tube 362 through the drainage port(s) 390.

Figure 33C:
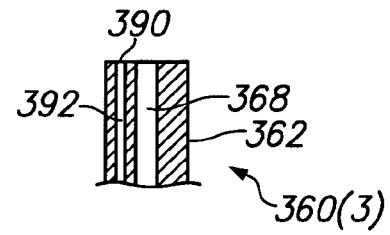
FIG. 33C is a cross-sectional detail of another variation of the de-endothelialization fluid delivery device of FIG. 33A.

FIG. 33A shows that the drainage port 390 is located transversely at a wall of the delivery tube 362. However, the drainage port 390 may also be located elsewhere. As shown in FIG. 33C, the drainage port 390 may also be located at the distal tip of the delivery tube 362. It should be noted that the number of drainage ports 390 may vary. Furthermore, the usage of the lumen 368 of the delivery tube 362 and the lumen 392 may interchange. In an alternative embodiment, the lumen 392 may be used to delivery fluid 350 to an aneurysm, and the lumen 368 of the delivery tube 362 may be used to drain or aspirate fluid 350 from the aneurysm.

Figure 33D:
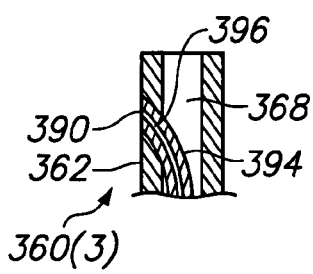
FIG. 33D is a cross-sectional detail of yet another variation of the de-endothelialization fluid delivery device of FIG. 33A including an inner tube.

The previously illustrated embodiments show that the drainage lumen 368 is defined within the wall of the delivery tube 362. Alternatively, as shown in FIG. 33D, the delivery tube 362 may include an inner tube 394 placed coaxially within the lumen 368 of the delivery tube 362. The inner tube 394 has a lumen 396 that is in fluid communication with one or more drainage ports 390 located at the distal end 364 of the delivery tube 362. Excess fluid 350 from the aneurysm may be drained into the drainage port 390 and delivered to a proximal end via the lumen 396 of the inner tube 394. Alternatively, the inner tube 394 may be used to deliver fluid 350 to the aneurysm and the lumen 368 of the delivery tube 362 may be used to aspirate excess fluid 350 from the aneurysm to a proximal end of the tube 362.

Figure 34A:
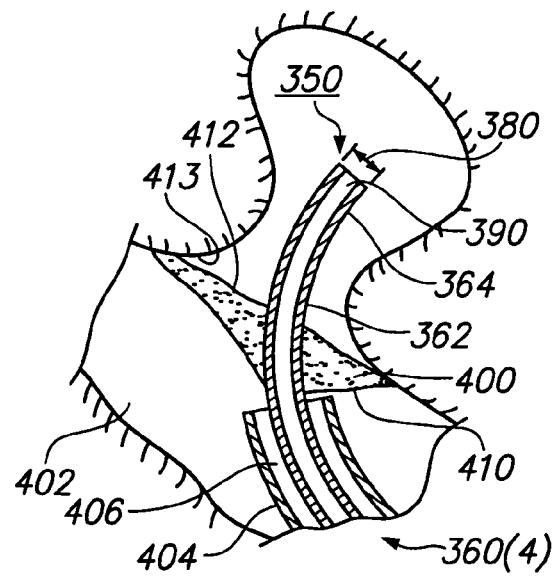
FIG. 34A is a cross-sectional detail of another variation of the de-endothelialization fluid delivery device of FIG. 32 including a stopper.

FIG. 34A shows another de-endothelialization fluid delivery device 360(4) that includes the delivery tube 362 and a sealing member or stopper 400 secured to the distal end 364 of the delivery tube 362. The device 360(4) may include one or more drainage ports (not shown) in accordance with any of the embodiments described above. The stopper 400 is used to substantially seal the aneurysm, i.e., to prevent or reduce the risk of having fluid 350 delivered into the aneurysm from escaping into the artery or vein 402. As such, the diameter 380 of the delivery tube 362 may be substantially the same or smaller than a diameter of the aneurysm, as discussed previously with reference to FIG. 32. If the delivery tube 362 has a diameter that is substantially the same or slightly larger than a diameter of an aneurysm, then the stopper 400 may function as a back-up device for preventing excess fluid 350 from flowing into the artery or vein 402. The stopper 400 is preferably made of a compressible or collapsible material, such as rubber or a foam-like material. However, other materials may also be used. The stopper 400 should have a shape and dimension such that it may substantially engage tissue around the neck of the aneurysm to substantially seal the aneurysm and prevent substantial leakage of fluid 350 into the artery or vein 402.

Figure 34B:
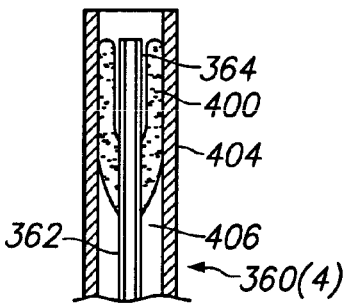
FIG. 34B is a detail of the de-endothelialization fluid delivery device of FIG. 34A, showing the stopper in a low profile disposed within a sheath.
Figure 34C:
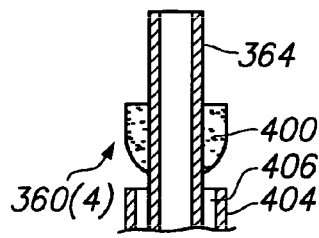
FIG. 34C is a detail of a variation of the de-endothelialization fluid delivery device of FIG. 34A including a stopper.
Figure 34D:
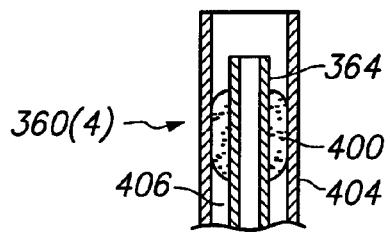
FIG. 34D is a detail of the de-endothelialization fluid delivery device of FIG. 34C, showing the stopper compressed into a low profile within a sheath.

The de-endothelialization fluid delivery device 360(4) may optionally include a sheath 404 having a lumen 406. As shown in FIG. 34B, the sheath 404 is capable of surrounding the distal end 364 of the delivery tube 362 such that the stopper 400 assumes a folded configuration when disposed within the lumen 406 of the sheath 404. Depending on the geometry of the stopper 400, the stopper 400 may also assume a compressed configuration when disposed within the lumen 406 of the sheath 404 (FIGS. 34C and 34D).

When using the de-endothelialization fluid delivery device 360(4), the sheath 404 is first inserted into an artery or vein and advanced until the distal end of the sheath 404 is adjacent an aneurysm. The sheath 404 may be advanced over a guide wire or other rail, as is known in the art. The delivery tube 362 may be placed initially within the lumen 406 of the sheath 404 and the sheath 404 together with the delivery tube 362 may then be positioned adjacent the aneurysm. Alternatively, the delivery tube 362 may be inserted into the lumen 406 of the sheath 404 after the sheath 404 is desirably placed. The stopper 400 may assume a bent and/or compressed configuration when disposed within the lumen 406 of the sheath 404.

Figure 34E:
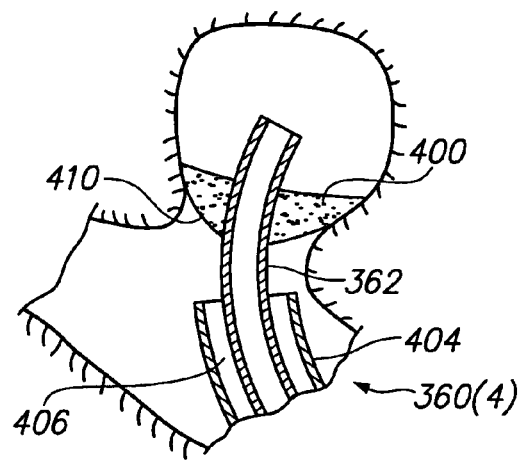
FIG. 34E is a partial cross-sectional side view of the de-endothelialization fluid delivery device of FIG. 34A, showing the stopper being deployed within an aneurysm.

The stopper 400 may be deployed, e.g., by retracting the sheath 404 relative to the tubular element 362, or by advancing the delivery tube 362 relative to the sheath 404. As shown in FIG. 34A, the stopper 400 may be deployed directly outside the neck of the aneurysm such that a distal side 412 of the stopper 400 engages with a vessel wall 413 directly outside the aneurysm so that the neck of the aneurysm is substantially sealed by the stopper 400. Alternatively, as shown in FIG. 34E, the stopper 400 can be deployed inside the neck of the aneurysm such that the proximal side 410 of the stopper 400 engages with the endothelium of the aneurysm.

The fluid 350 is then delivered to the aneurysm from the fluid supply 310. After the fluid 350 contacts the endothelium of the aneurysm, the de-endothelialization property of the fluid 350 causes the endothelium of the aneurysm to be disrupted. The neck of the aneurysm is substantially sealed by the stopper 400 during the process such that fluid 350 may be drained or aspirated via a drainage port 390 without substantial leaking from the aneurysm into the artery or vein 402. After a desired amount of the fluid 350 has been delivered and/or aspirated, the delivery tube 362 and the stopper 400 are then withdrawn back into the lumen 406 of the sheath 404.

Figure 34F:
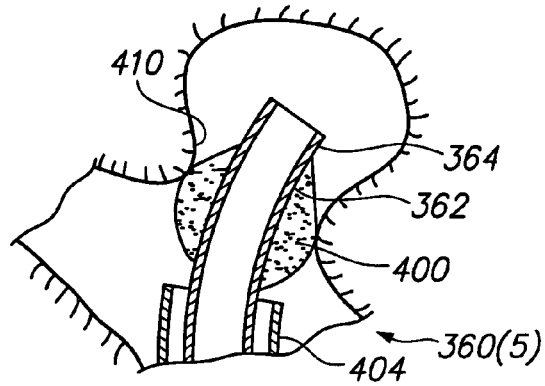
FIG. 34F is a cross-sectional side view of a variation of the de-endothelialization fluid delivery device of FIG. 34A, showing a stopper having an elliptical shape.

The shape of the stopper 400 should not be limited to the examples shown previously and that the stopper 400 may have other shapes. FIG. 34F shows a de-endothelialization fluid delivery device 360(5) that includes a stopper 400 having an elliptical shape. When using the de-endothelialization fluid delivery device 360(5), a portion of the stopper 400 may be inserted into the aneurysm until the stopper 400 bears against a surface 410 that defines the neck of the aneurysm. If desired, the distal end 364 of the delivery tube 362 may be advanced a relatively small increment to compress the stopper 400 within the neck of the aneurysm. This has the benefit of ensuring that the neck of the aneurysm is substantially sealed by the stopper 400. The fluid 350 is then delivered into the aneurysm, as discussed previously. Fluid 350 delivered to the aneurysm may be aspirated or otherwise drained into a drainage port (now shown), the stopper 400 substantially preventing the fluid 350 from leaking from the aneurysm, as discussed previously.

Figure 35:
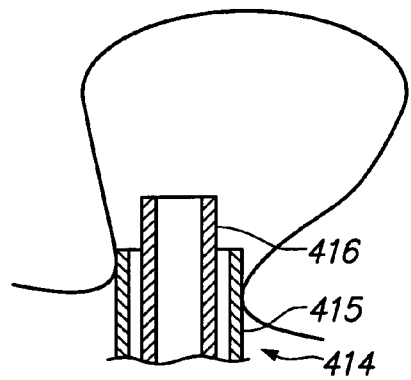
FIG. 35 is a partial cross-sectional side view of an alternative embodiment of a de-endothelialization fluid delivery device.

FIG. 35 shows a de-endothelialization fluid delivery device 414 in accordance with another embodiment of the present invention. The de-endothelialization fluid delivery device 414 includes an outer tubular element 415 and an inner tubular element 416 slidable within a lumen of the outer tubular element 415. The outer tubular element 415, which is preferably a micro-catheter or a sheath, may have a diameter that is the same or slightly larger than the neck of an aneurysm, as discussed previously with reference to FIG. 32. The proximal end of the inner tubular element 416 may be coupled to a source of de-endothelialization fluid (not shown).

When using the de-endothelialization fluid delivery device 414, the distal tip of the outer tubular element 415 is first placed within the neck of an aneurysm or other body lumen, as shown in FIG. 35. The outer tubular element 415 may be placed and/or positioned using similar methods to those discussed previously, e.g., with reference to FIG. 32, or by conventionally known techniques. The inner tubular element 416 may be disposed within the lumen of the outer tubular element 415 and delivered together with the outer tubular element 415 to a target site. Alternatively, the inner tubular element 416 may be inserted into the lumen of the outer tubular element 415 after the outer tubular element 415 is desirably situated, and then advanced distally until it reaches the distal end of the outer tubular element 415. Either or both of the outer and inner tubular elements may include one or more radio-opaque markers (not shown) at their respective distal ends for facilitating positioning the tubular elements.

When both the outer and inner tubular elements 415 and 416 are desirable positioned, de-endothelialization fluid is then delivered into the aneurysm or other body lumen via the inner tubular element 416. Depending upon the size and geometry of the aneurysm or other body lumen, the inner tubular element 416 may be advanced and/or retracted relative to the outer tubular element 415 at various positions during and/or before delivering the de-endothelialization fluid. Excess de-endothelialization fluid may be aspirated or drained by the outer tubular element 415 during and/or after the delivery of the de-endothelialization fluid. After a desired amount of de-endothelialization has been delivered, the outer and inner tubular elements 415 and 416 are then withdrawn from the target site.

Figure 36:
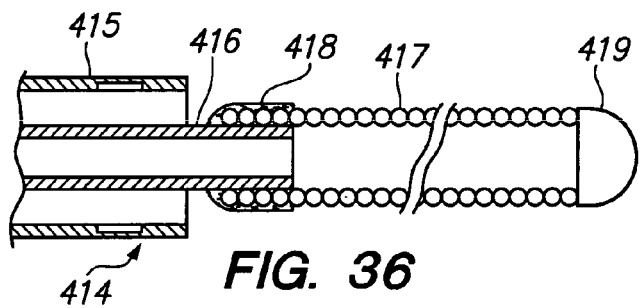
FIG. 36 is a partial cross-sectional side view of a variation of the de-endothelialization fluid delivery device of FIG. 35.

The de-endothelialization fluid delivery device 414 may further include a coil 417 secured to the distal end of the inner tubular element 416, such as that shown in FIG. 36, to disperse the injected fluid within the aneurysm or other body lumen. The coil 417 is not limited to the linear shape shown in the illustrated embodiment, and may have other shapes as well. In particular, the coil 417 may have any of the secondary shapes discussed previously with reference to FIGS. 5-11. The coil 417 is preferably made from a radio-opaque material, such as platinum. However, other materials such as stainless steel, aluminum, and/or plastic, may also be suitable for constructing the coil 417. Generally, any of the materials discussed previously with reference to the core member 12 may also be used. The length of the coil 417 is preferably from about two millimeters (2 mm) to about three hundred millimeters (300 mm). The coil 417 may also have other lengths, depending on the particular application. The spacing between the windings of the coil 417 may vary. Generally, smaller spacing between the windings may better disperse the de-endothelialization fluid.

Figure 37:
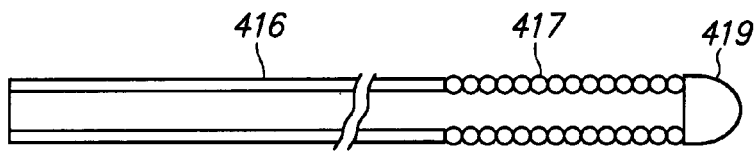
FIG. 37 is a partial cross-sectional side view of a variation of the de-endothelialization fluid delivery device of FIG. 36.

In the illustrated embodiment, the coil 417 is secured to the distal end of the inner tubular element 416 by an epoxy 418. Other suitable adhesives may also be used. As shown in FIG. 36, the proximal end of the coil 417 fits around the distal end of the inner tubular element 416. Alternatively, the proximal tip of the coil 417 may abut and be secured to the distal tip of the inner tubular element 416, as shown in FIG. 37. The de-endothelialization fluid delivery device 414 may further include an atraumatic tip 419 secured to the distal end of the coil 417.

When using the de-endothelialization fluid delivery device 414 of FIG. 36 in an aneurysm, the distal end of the outer tubular element 415 is first placed within the neck of then aneurysm, as discussed previously, e.g., with reference to FIG. 35. The inner tubular element 416 is then advanced within the lumen of the outer tubular element 415 until the coil 417 extends at least partially beyond the distal end of the outer tubular element 415 and into the aneurysm. If the coil 417 has a secondary shape or configuration, it may attempt to return towards the secondary shape as it is deployed from the lumen of the outer tubular element 415. De-endothelialization fluid may then be delivered via the inner tubular element 416 into the lumen of the coil 417, where it may escape through spaces between the windings of the coil 417. The windings of the coil 417 may disperse the de-endothelialization fluid within the aneurysm. De-endothelialization fluid may then be aspirated or drained by the outer tubular element 415. When a desired amount of the de-endothelialization fluid has been delivered and/or aspirated, the outer and inner tubular elements 415 and 416 may then be withdrawn from the treatment site.

It should be understood by those skilled in the art that the outer tubular element 415 discussed previously with reference to FIGS. 35-37 is primarily used to aspirate excess delivered de-endothelialization fluid, and that, optionally, it may be eliminated (or if provided, it may not necessarily be placed within the neck of the aneurysm) if the de-endothelialization fluid may be mixed safely with blood. In this case, the de-endothelialization fluid may leak out of the sac of the aneurysm without being aspirated or drained by the outer tubular element 415.

Figure 38A:
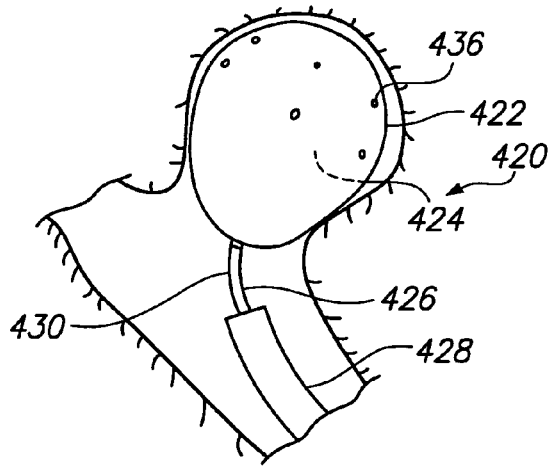
FIG. 38A is a partial side view of a de-endothelialization fluid delivery device including a balloon deployed within an aneurysm.
Figure 38B:
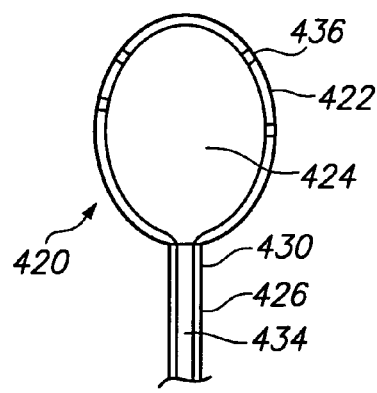
FIG. 38B is a cross section of the de-endothelialization fluid delivery device of FIG. 38A.

FIG. 38A shows a de-endothelialization fluid delivery device 420 that includes a balloon 422 having a lumen 424 (shown in FIG. 38B), a delivery tube 426, and a sheath 428. The sheath 428 preferably has a diameter or cross-sectional dimension that is the same or slightly larger than that of a neck of an aneurysm so that it can be used to aspirate de-endothelialization fluid from the aneurysm, as discussed previously with reference to the outer tubular element 415 in FIGS. 35-37. The balloon 422 is preferably made of a compliant material, such as silicone, rubber, low density polyethylene, high density polyethylene, polypropylene, polybutene, interpolymers or mixtures of these polymers, so that when it is inflated, it may conform to the shape of an aneurysm. In general, any of the materials discussed previously with reference to the balloon 170 of FIG. 25A is also applicable for constructing the balloon 422. The balloon 422 is not limited to the shape shown in the illustrated embodiment, and may have other shapes as well.

The delivery tube 426 includes a distal end 430, a proximal end 432 (not shown), and a lumen 434 (FIG. 38B) extending between the distal end 430 and the proximal end 432. The distal end 430 of the delivery tube 426 is coupled to the balloon 422 such that the lumen 424 of the balloon 422 communicates with the lumen 434 of the delivery tube 426. The balloon 422 includes one or more openings 436 that communicate with the lumen 424 of the balloon 422. The opening 436 has a size such that, when the balloon 422 is inflated by fluid, the opening 436 may expand sufficiently to allow fluid to exit the balloon 422.

Figure 39A:
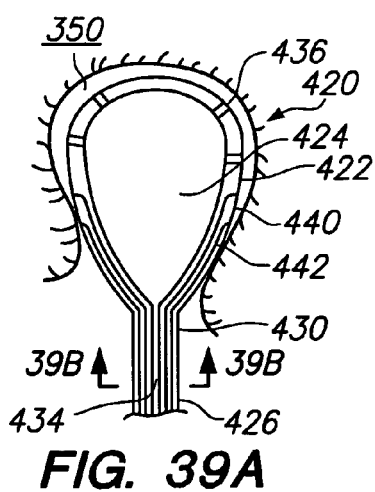
FIG. 39A is a cross-sectional view of a variation of the de-endothelialization fluid delivery device of FIG. 38A including a balloon having a drainage port.
Figure 39B:
FIG. 39B is a cross sectional view of the delivery tube of the de-endothelialization fluid delivery device of FIG. 39A taken along line 39B-39B.
Figure 40A:
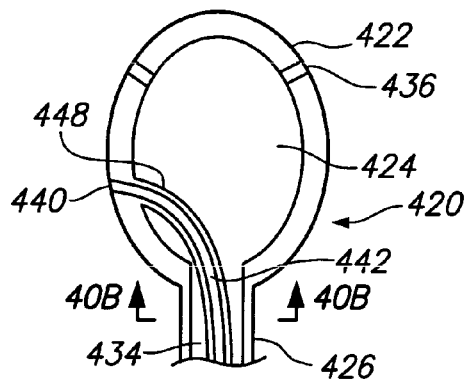
FIG. 40A is a cross section of a variation of the de-endothelialization fluid delivery device of FIG. 39A including a drainage port coupled to a drainage tube.
Figure 40B:
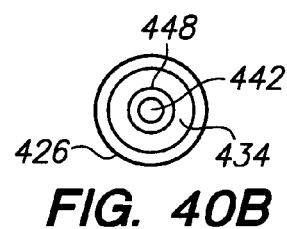
FIG. 40B is a cross sectional view of the delivery tube of the de-endothelialization fluid delivery device of FIG. 40A taken along line 40B-40B.

As shown in FIG. 39A, the de-endothelialization device 420 may further include one or more drainage ports 440 located at a surface of the balloon 422, through which fluid 350 may be aspirated and delivered back to a proximal end (not shown) of the delivery tube 426 via a drainage lumen 442. FIG. 39B is a cross sectional view of the delivery tube 426, showing the drainage lumen 442 inside a wall of the delivery tube 426. FIGS. 40A and 40B show a variation of the de-endothelialization fluid delivery device 420 in which the drainage lumen 442 is a separate drainage tube 448 surrounded by the delivery tube 428. It should be noted that the location and number of drainage ports 440 and the shape of the balloon may vary, and that they should not be limited to the examples shown in the illustrated embodiments.

Figure 41:
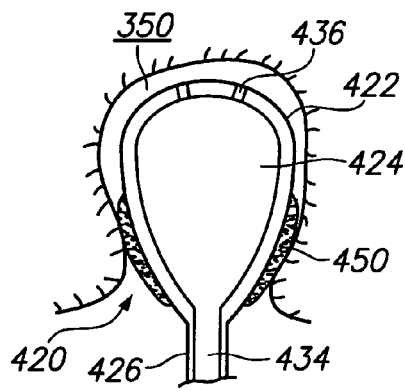
FIG. 41 is a cross-sectional view of a variation of the de-endothelialization fluid delivery device of FIG. 38A including a stopper.

FIG. 41 shows another variation of the de-endothelialization fluid delivery device 420 that includes a sealing member or stopper 450 secured to the balloon 422. Although the illustrated embodiment shows that the stopper 450 extends above the surface of the balloon 422, the stopper 450 may also be constructed such that it is flush with the surface of the balloon 422. The stopper 450 may have a variety of shapes, and is not limited to the planar configuration shown in the illustrated embodiment. Furthermore, the stopper 450 may be secured to the distal end of the delivery tube 428 (not shown, see FIG. 38A) instead of to the balloon 422 so long as the stopper 450 is capable of sealing the neck of the aneurysm to prevent fluid 350 from leaving the aneurysm. In general, any of the materials discussed previously with reference to the stopper 400 may be used for the stopper 450.

When using the de-endothelialization fluid delivery device 420, the balloon 422 is inflated within the aneurysm by delivering fluid 350 via the delivery tube 426 into the lumen 424 of the balloon 422. When the balloon 422 is inflated to a certain size, the fluid 350 exits through the opening(s) 436 of the balloon 422 due to internal pressure within the balloon 422 and/or the size of the opening(s) 436 increasing as the balloon 422 expands. The fluid 350 then contacts the endothelium of the aneurysm, thereby disrupting the endothelium. If the de-endothelialization fluid delivery device 420 includes a drainage port 440, it may be used to aspirate fluid 350 from within the aneurysm. Alternatively, if the de-endothelialization fluid delivery device 420 includes a stopper 450, the stopper 450 may be used to absorb fluid 350 within the aneurysm. When the de-endothelialization process is complete, the balloon 422 may be deflated and removed from the aneurysm.

Figure 42:
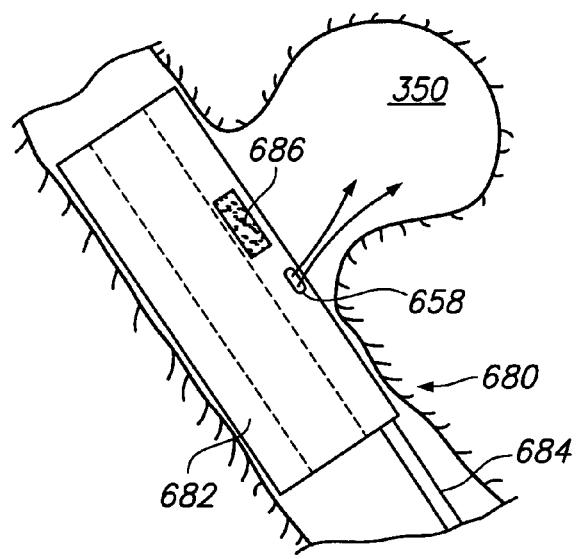
FIG. 42 is a side view of a de-endothelialization fluid delivery device including a triple-lumen catheter.
Figure 42A:
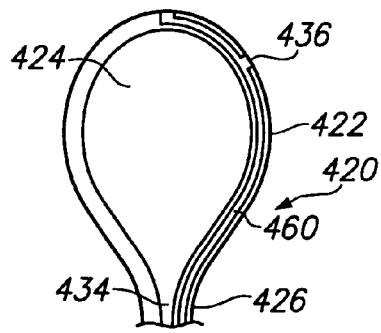
FIG. 42A is a cross-sectional view of another variation of the de-endothelialization fluid delivery device of FIG. 38A, including a fluid delivery lumen formed within a wall of the balloon for delivering de-endothelialization fluid.
Figure 42B:
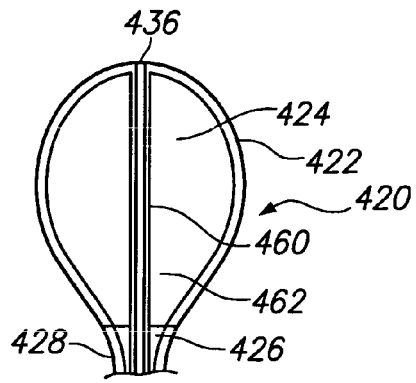
FIG. 42B is a cross-sectional view of another variation of the de-endothelialization fluid delivery device of FIG. 38A including a separate tube coaxially surrounded by the delivery tube.

FIG. 42A shows another variation of the de-endothelialization fluid delivery device 420 that includes a separate delivery lumen 460 for delivering fluid to an aneurysm. In this case, the delivery tube 426 (not shown, see FIG. 38A) may be used to deliver an inflation fluid, such as water, saline, blood, and/or de-endothelialization fluid 350 to the lumen 424 of the balloon 422 to inflate the balloon 422. After the balloon 422 has been inflated to a desired size, the de-endothelialization fluid may be delivered via the delivery lumen 460 to the aneurysm. FIG. 42A shows that the delivery lumen 460 is formed within a wall of the delivery tube 428. Alternatively, as shown in FIG. 42B, a separate tube 462 may provide the delivery lumen 460. The tube 462 is coaxially surrounded by the delivery tube 428. In either case, the de-endothelialization device 420 may optionally include a drainage port 440 or a stopper 450 as discussed previously.

Figure 43A:
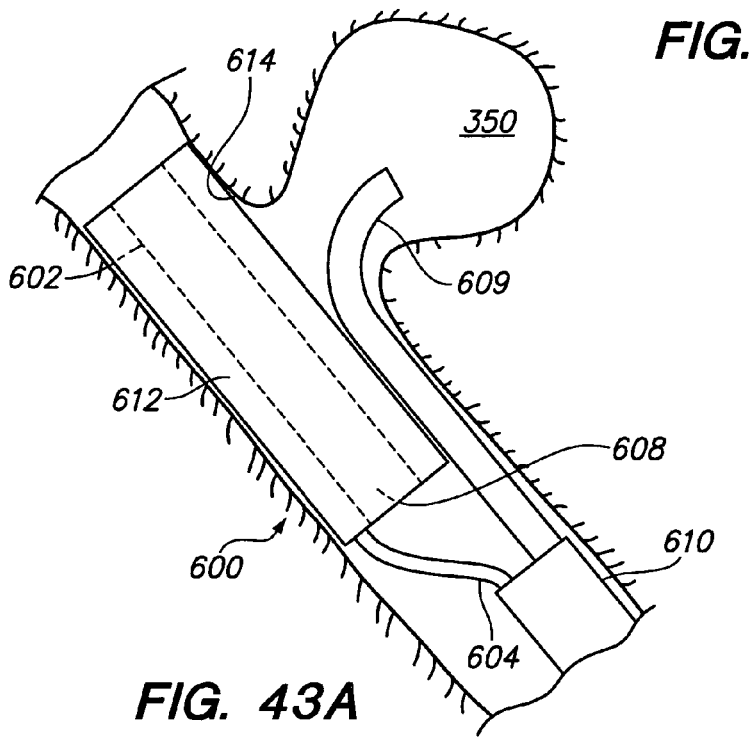
FIG. 43A is a side view of a de-endothelialization system including a perfusion balloon.

Optionally, any of the de-endothelialization fluid delivery devices described previously with reference to FIGS. 31-42B may be used with a perfusion balloon 600, such as that shown in FIG. 43A. The perfusion balloon 600 has a lumen 602, and is coupled to an inflation tube 604 such that the lumen 602 of the perfusion balloon 600 is in fluid communication with a lumen of the inflation tube 604. The perfusion balloon 600 has a shape such that when it is inflated, it defines an opening 608 for allowing blood to flow through the perfusion balloon 600. The perfusion balloon 600 is preferably made of an elastic material, such as a polymer. In general, any of the materials discussed previously with reference to the balloon 170 of FIG. 25A may also be used. However, other materials may also be used.

Before using the perfusion balloon 600, a de-endothelialization fluid delivery device 609 is first placed adjacent or within an aneurysm. The de-endothelialization fluid delivery device 609 is representative of any of the de-endothelialization fluid delivery devices described previously with reference to FIGS. 31-42B. When using the perfusion balloon 600, the perfusion balloon 600 is delivered to a site where the aneurysm is located. A sheath 610 may be used to deliver the perfusion balloon 600. If the de-endothelialization device 609 includes a sheath, the sheath of the de-endothelialization device may also be used instead to deliver the perfusion balloon 600. The perfusion balloon 600 is collapsed and assumes a low profile when disposed within the lumen of the sheath.

Once the sheath 610 is adjacent the aneurysm, the perfusion balloon 600 is deployed from the distal end of the sheath, either by distally advancing the perfusion balloon 600 relative to the distal end of the sheath 610, or by retracting the sheath 610 relative to the perfusion balloon 600. An inflation fluid, such as saline, water, blood, or gas is then delivered by the inflation tube 604 to within the lumen 602 of the perfusion balloon 600, thereby expanding the perfusion balloon 600 until a surface 612 of the perfusion balloon 600 engages the vessel wall 614. As shown in FIG. 43A, when the perfusion balloon 600 is inflated, it forms a barrier substantially sealing the neck of the aneurysm, thereby reducing the chance that fluid 350 delivered into the aneurysm may escape into the vessel or artery.

Figure 43B:
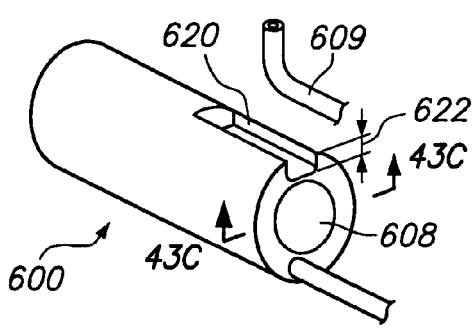
FIG. 43B is a perspective view of a variation of the perfusion balloon of the de-endothelialization system of FIG. 43A.
Figure 43C:
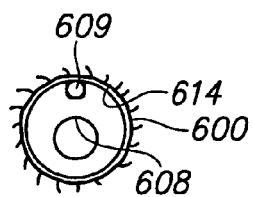
FIG. 43C is a cross sectional view of the perfusion balloon of FIG. 43B taken along line 43C-43C.

FIG. 43B shows a variation of the perfusion balloon 600 that includes a slot 620 in which a portion of the de-endothelialization fluid delivery device 609 may be placed. The slot 620 preferably has a depth 622 that is substantially the same as a diameter of the de-endothelialization fluid delivery device 609. This may allow the de-endothelialization fluid delivery device 609 to form a substantially continuous surface with the perfusion balloon 600 to better engage the wall 614 of the vessel or artery, as shown in FIG. 43C.

Figure 44A:
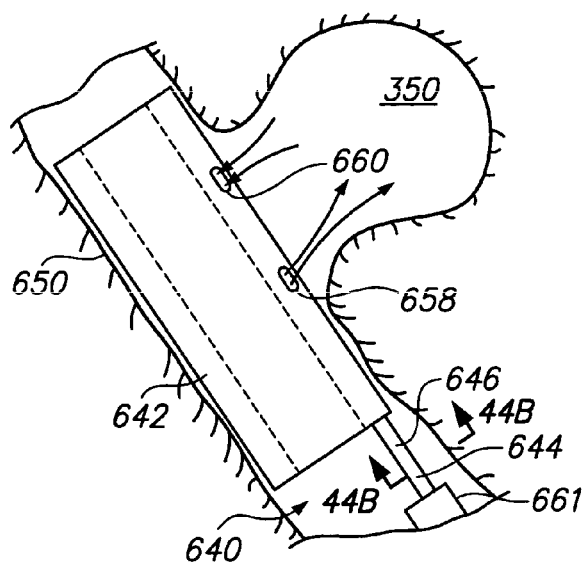
FIG. 44A is a side view of a de-endothelialization fluid delivery device including a triple-lumen catheter.
Figure 44B:
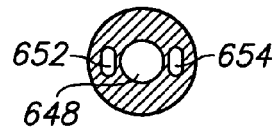
FIG. 44B is a cross sectional view of the triple-lumen catheter of FIG. 44A taken along line 44B-44B.

FIG. 44A shows a de-endothelialization fluid delivery device 640 that includes a balloon 642 and a triple-lumen catheter 644. The balloon 642 is coupled to a distal portion 646 of the triple-lumen catheter 644. As shown in FIG. 44B, the triple-lumen catheter 644 includes a first lumen 648 that communicates with a lumen 650 of the balloon 642, a second lumen 652 for delivering de-endothelialization fluid 350 to an aneurysm, and a third lumen 654 for aspirating fluid 350 from the aneurysm. It should be noted that the association of specific lumens with respective purposes is merely a matter of design choice, and that any of the lumens 648, 652, and 654 may be used for inflating the balloon 642, delivering fluid 350, and draining fluid. The balloon 642 includes one or more openings 658 communicating with the second lumen 652 of the triple-lumen catheter 644, and one or more drainage ports 660 communicating with the third lumen 654 of the triple-lumen catheter 644. The balloon 642 preferably has a tubular shape, e.g., similar to the perfusion balloon 600 discussed previously, such that blood may continue to flow through the vein or artery while the fluid 350 is being delivered to the aneurysm. The de-endothelialization fluid delivery device 640 may further include a sheath 661.

Figure 44C:
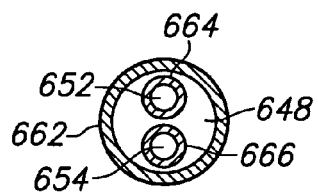
FIG. 44C is a cross-sectional view of a variation of the triple-lumen catheter of FIG. 44A.
Figure 44D:
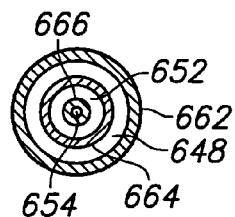
FIG. 44D is a cross-sectional view of another variation of the triple-lumen catheter of FIG. 44A.

The triple-lumen catheter 644 is not necessarily limited to the configuration described previously. FIG. 44C shows a variation of the triple-lumen catheter 644 that includes a first tube 662 defining the first lumen 648, a second tube 664 defining a second lumen 652, and a third tube 666 defining a third lumen 654. The first tube 662 coaxially surrounds the second tube 664 and the third tube 666. FIG. 44D shows another variation of the triple-lumen catheter 644 in which the first tube 662 surrounds the second tube 664, and the second tube 664, in turn, surrounds the third tube 666.

When using the de-endothelialization fluid delivery device 640, the balloon 642 is first placed adjacent to a neck of the aneurysm. The balloon 642 may be delivered using a sheath 661 and/or a guide wire, as is known in the art. For example, the sheath 661 may be advanced over a guide wire (not shown) through a vasculature until the distal end of the sheath 661 is adjacent to the neck of the aneurysm. The balloon 642 coupled to the triple-lumen catheter 644 may then be deployed from the lumen of the sheath 661, e.g., by advancing the balloon 642 into the lumen from the proximal end of the sheath 661 until it emerges at the distal end of the sheath 661.

Before and/or after the balloon 642 exits the lumen of the sheath 661, if required, the position and/or the orientation of the balloon may be adjusted by advancing, retracting, and/or rotating the proximal end of the triple-lumen catheter 644, until the openings 658 and 660 of the balloon 642 face the opening of the aneurysm. The balloon 642 is then inflated by a media, such as saline, a gas, or other fluid. The balloon 642 substantially closes the neck opening of the aneurysm while allowing blood to flow through the vein or artery. Next, de-endothelialization fluid 350 may be delivered through the second lumen 652 of the triple-lumen catheter 644 into the aneurysm. If the de-endothelialization fluid delivery device 640 includes a drainage port 660, fluid 350 may be aspirated from the aneurysm via then port 660. After a desired amount of the fluid 350 has been delivered, the balloon 642 is then deflated and withdrawn into the lumen of the sheath 661.

Figure 45:
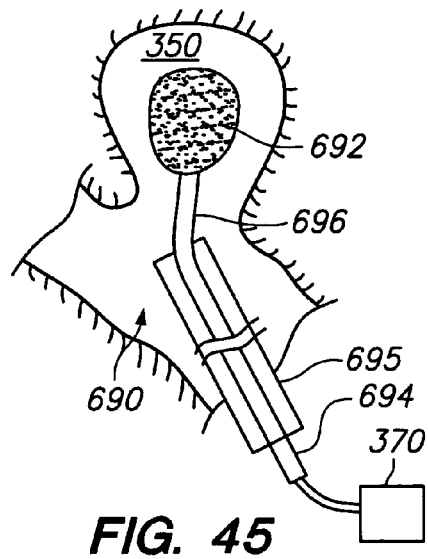
FIG. 45 is a side view of a de-endothelialization fluid delivery device including an expandable applicator deployable from a delivery sheath.
Figure 46:
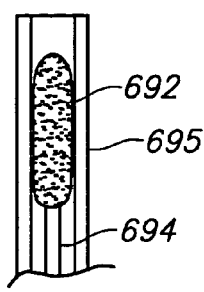
FIG. 46 is a partial cross-sectional view of the de-endothelialization fluid delivery device of FIG. 45, showing the applicator compressed into a low profile within the sheath.

FIG. 45 shows another de-endothelialization fluid delivery device 690 that includes an applicator 692, a tube 694, and a sheath 695. The applicator is coupled to a distal end 696 of the tube 694, and is capable of being compressed into a low profile when disposed within the lumen of the sheath 695 (FIG. 46). The applicator 692 is made of a porous and/or absorptive material, e.g., similar to a sponge. The tube 694 also has a proximal end 698 that is coupled to the fluid source 370. When using the de-endothelization device 690, the applicator 692 is first deployed into an aneurysm. De-endothelialization fluid 350 is then delivered via the tube 694 to the applicator 692. Alternatively, the applicator 692 may also be deployed into the aneurysm after the fluid 350 is delivered to the applicator 692. The applicator 692 controls the amount of fluid 350 that may be delivered to the aneurysm, thereby reducing the risk of having excess fluid 350 flowing from the aneurysm to an artery or vessel. It should be noted that applicator 692 may have other shapes and/or that other types of applicators known in the art may also be used.

Turning to FIGS. 52A-52E, a system 810 is shown for treating an aneurysm 90 extending from a body lumen, such as a cerebral artery or other blood vessel 92. Generally, the system 810 includes an outer tubular member 812 including a proximal end (not shown), a distal end 814 having a size and shape for insertion into the aneurysm 90, and a lumen 816 extending between the proximal end and distal end 814. The system 10 also includes an inner tubular member 822 disposed within the outer tubular member 812 that also includes a lumen 826. The inner tubular member 822 may be slidable relative to the outer tubular member 812, e.g., to retract or expose a distal end 824 of the inner tubular member 822, as will be appreciated by those skilled in the art.

The inner tubular member 822 is substantially smaller than the outer tubular member 812 such that the lumen 816 between the inner and outer tubular members 822, 812 has a generally annular cross-section. The lumen 826 within the inner tubular member 822 may be coupled to a source of fluid (not shown), thereby providing an infusion lumen, while the annular lumen 816 may be coupled to a source of vacuum (also not shown), thereby providing an aspiration lumen. Alternatively, the functions of these lumens 816, 826 may be reversed or they may coupled to other components, as will be appreciated by those skilled in the art.

Figure 52A:
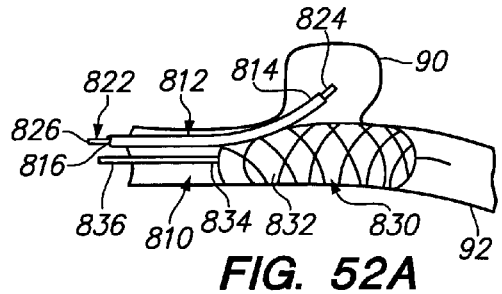
FIGS. 52A-52E show a blood vessel with an aneurysm being treated using a dual catheter system, in accordance with the present invention.
Figure 52B:
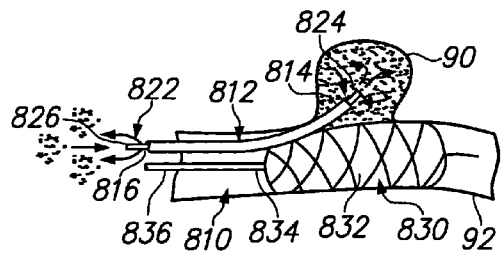
Figure 52C:
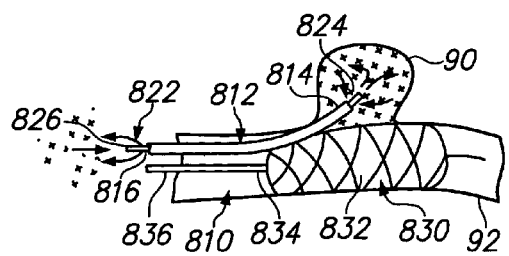
Figure 52D:
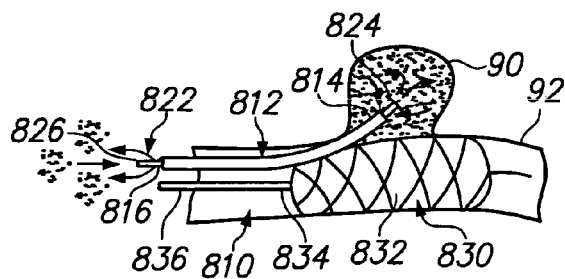
Figure 52E:
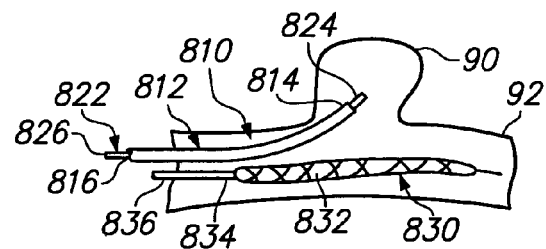
Figure 53:
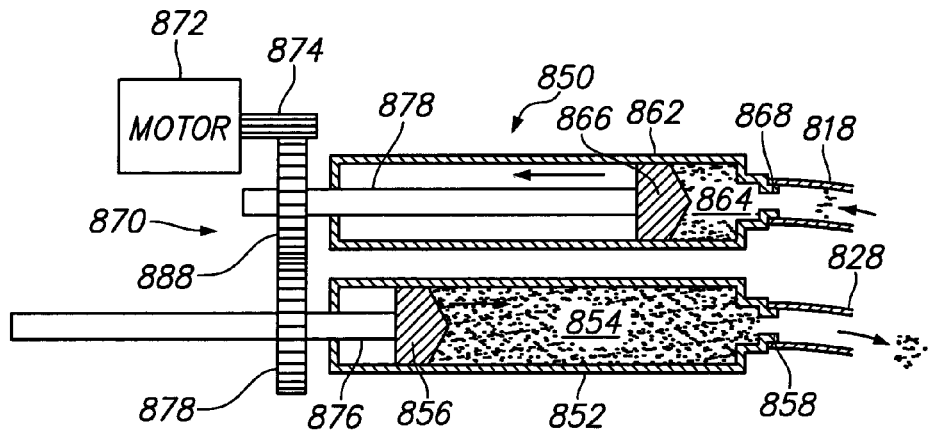
FIG. 53 is a cross-sectional side view of a dual syringe system for simultaneously injecting and aspirating fluid, in accordance with the present invention.

Turning to FIG. 53, a dual syringe apparatus 850 is shown that may be coupled to the inner and/or outer tubular members 822, 812 shown in FIGS. 52A-52E, e.g., by tubing 818, 828. Generally, the apparatus 850 includes first and second syringe barrels 852, 862 including first and second chambers 854, 864 and first and second pistons 856, 866, respectively. The barrels 852, 862 may have similar cross-sections or different cross-sections, depending upon whether the delivery and aspiration should be the same or different from one another. The first and second pistons 856, 866 are movable within the first and second chambers, respectively, for delivering fluid and/or for aspirating fluid, as explained further below. In addition, the first barrel 852 includes an outlet port 858 and the second barrel 862 has an inlet port 868 to which tubing 828, 818 may be connected using conventional methods, e.g., luer lock connectors and the like (not shown).

The system 850 also includes an actuator 870 for moving the first piston 856, e.g., to deliver fluid within the first chamber 854, and/or for moving the second piston 866, e.g., to aspirate fluid into the second chamber 864. In the preferred embodiment shown, the actuator 870 includes a motor 872 with an output shaft 874 that is coupled to shafts 876, 886, e.g., via sprockets or wheels 878, 888. Preferably, the wheels 878, 888 are coupled to one another such that, when the motor 872 is operated, the output shaft 874 simultaneously rotates the wheels 878, 888, thereby simultaneously advancing and retracting the pistons 856, 866, respectively. It will be appreciated that other actuators may also be provided that may be operated manually and/or automatically, instead of the motor and shaft arrangement shown in FIG. 53. In addition, the volumetric rates of fluid delivery and fluid aspiration need not be the same.

It will be appreciated that other fluid moving elements may be provided in addition to or instead of the dual syringes described above. For example a fluid delivery pump and as aspiration pump may be coupled to the delivery and aspiration lumens and to an actuator for simultaneously delivering and aspirating fluid, as described elsewhere herein.

Returning to FIGS. 52A-52E, optionally, the system 810 may include an occlusion member 830 for substantially sealing the aneurysm 90 from the vessel 92. In the embodiment shown, the occlusion member 830 includes an expandable member 832 carried on a distal end 834 of an elongate member 836. In a preferred embodiment, the expandable member 832 is a compliant, nonporous balloon and the elongate member 836 is a catheter or micro-catheter including an inflation lumen for infusing fluid into and/or aspirating fluid from the balloon. Alternatively, a mechanically expandable member (not shown) or other sealing member may be provided. In a further alternative, an expandable member (not shown) may be provided proximate to the distal end of the outer tubular member 812, rather than on a separate member.

In other alternatives, similar to the embodiment described above, the inner member may be eliminated, and the outer tubular member may include two lumens, one for infusion and one for aspiration (not shown). The lumens may be arranged coaxially, side-by-side, or in any other configuration. The distal end of the outer tubular member may include one or more ports spaced apart from one another in a desired arrangement, with one or more ports communicating with respective lumens.

In yet another alternative, the expandable member may include one or more ports, and the elongate member may include one or more additional lumens communicating with respective ports, e.g., for infusing or aspirating fluid, similar to the embodiments described above with reference to FIG. 44A. This may allow the inner tubular member to be eliminated, while only requiring the outer tubular member to include one lumen, or may even allow both tubular members to be eliminated.

Returning to FIGS. 52A-52E, a method is shown for treating a malformation, such as an aneurysm 90, extending from a body lumen, such as a blood vessel 92. Initially, the outer tubular member 812 may be introduced into the patient's vasculature, e.g., from a percutaneous entry site, and advanced over a guidewire (not shown) until the distal end 814 is located within the aneurysm 90. The outer tubular member 812 may include a substantially rounded and/or atraumatic tip to facilitate advancing the outer tubular member 812 through tortuous anatomy, as is well known in the art.

The occlusion member 830 may be advanced into the vessel 92 until the expandable member 832 is disposed adjacent the aneurysm 90. The occlusion member 830 may be delivered within a catheter, sheath, or other device, e.g., to protect the expandable member 832 and/or the patient. Once the expandable member 832 is properly positioned, it may be expanded to substantially seal the aneurysm 90 from the vessel 92, as shown in FIG. 52A. Preferably, the expandable member 832 substantially engages the outer tubular member 812, e.g., to enhance the seal against the vessel 92 and/or to prevent axial movement of the outer tubular member 812 relative to the aneurysm 90.

Material, such as blood, other fluid, and/or particulate, may be aspirated from aneurysm, e.g., to substantially clear the interior of the aneurysm 90. Preferably, as shown in FIG. 52B, heparinized saline or other isotonic solution with or without a contrast agent is delivered, e.g., via the lumen 826 within the inner tubular member 822, into the aneurysm 90 to facilitate clearing the interior of the aneurysm 90. More preferably, the saline or other solution is infused into the aneurysm 90 substantially simultaneously with aspirating excess fluid, e.g., saline, solution, blood, and/or loose particulate, from the aneurysm 90, e.g., using an actuator such as the system 850 shown in FIG. 53.

Because of the occlusion member 830, the fluid being infused into and/or aspirated from the aneurysm 90 without leaking substantially into the vessel 92. In alternative embodiment, the occlusion member 830 may not be expanded to substantially seal the aneurysm 90 during the infusion and/or aspiration of fluid to clear the aneurysm, e.g., if the fluid is substantially harmless if it travels downstream in the vessel 92.

Turning to FIG. 52C, a therapeutic fluid may then be delivered into the aneurysm 90. The therapeutic fluid may be intended to cause a variety of reactions within the aneurysm 90, e.g., cellular lysis, disruption of cellular adhesions, and/or disruption of cellular function. For example, the therapeutic fluid may include distilled water, a hypo-osmotic solution, a hyper-osmotic solution, a detergent, a membrane disruptive polymer solution, and/or a membrane disruptive protein solution capable of causing cellular lysis within the wall of the aneurysm 90.

In addition or alternatively, the therapeutic agent may include a solution capable of disrupting intercellular adhesions, such as proteolytic enzymes (e.g., trypsin), or other agents that disrupt adhesive connections between cells. In a further alternative, the therapeutic fluid may include a solution capable of disrupting or ceasing one or more cellular functions, such as ethanol, a chemotherapeutic agent, a cytostatic agent, and/or a cytotoxic agent. Optionally, the therapeutic agent may include x-ray contrast, e.g., to identify when at least some therapeutic agent remains within the aneurysm 90.

As shown in FIG. 52D, once the therapeutic agent has had an opportunity to act within the aneurysm, the therapeutic fluid may be aspirated from the aneurysm. Preferably, fluid, such as saline or other isotonic solution with or without a contrast agent, is infused into the aneurysm 90 substantially simultaneously with aspirating excess fluid including the therapeutic fluid from the aneurysm. Alternatively, sufficient vacuum may be maintained such that the expandable member 852 may be at least partially collapsed, thereby allowing fluid from the vessel 92 to enter the aneurysm 90 and fill the void as fluid is aspirated.

Finally, as shown in FIG. 52E, once the therapeutic agent has been substantially removed from the aneurysm 90, the expandable member 832 may be collapsed, e.g., by aspirating the fluid infused into the expandable member 832. The outer tubular member 812, inner tubular member 822, and/or the occlusion member 850 may then be removed from the vessel 92 and from the patient's body, e.g., using conventional procedures.

Figure 54:
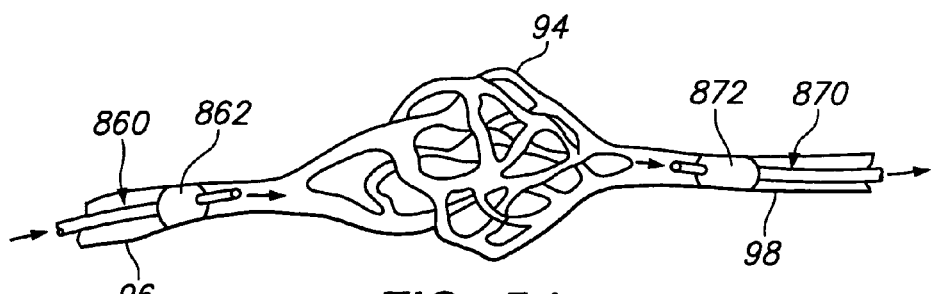
FIG. 54 shows an arterio-venous malformation being treated using a dual catheter system, in accordance with the present invention.

Turning to FIG. 54, a similar method is shown for treating an arterio-venous malformation 94 that extends between"an artery 96 and a vein 98. Unlike the previous embodiment, separate balloon catheters 860, 870 may be introduced into the artery 96 and the vein 98 using conventional methods. Once positioned as desired, balloons 862, 872 on the catheters 860, 870 may be expanded to engage the artery 96 and vein 98, respectively, thereby substantially isolating the malformation 94 from the artery 96 and vein 98.

Fluid within the malformation 94 may be aspirated, e.g., using the catheter 870 either alone or in conjunction with infusion of saline and the like, e.g., using the catheter 860. Thus, one catheter may be used for infusion while the other is used for aspiration. Optionally, the system 850 shown in FIG. 53 or other actuator may be used to infuse and aspirate substantially simultaneously, as described above. Once the malformation is sufficiently cleared, a therapeutic agent, similar to those described above, may be introduced, e.g., from one or both catheters. Optionally, excess fluid may be aspirated from the malformation 94 either during or after the therapeutic agent is introduced, similar to the method described above. Once the therapeutic agent has remained within the malformation 94 for sufficient time, the therapeutic agent may be aspirated, e.g., in conjunction with fluid infusion, similar to the previous embodiments. The balloons 862, 872 may be collapsed and the catheter 860, 870 removed from the artery 96 and vein 98.

Alternatively, a similar method may be used for introducing a de-endothelialization agent into other blood vessels. For example, a balloon catheter, similar to those described above may be introduced into a blood vessel adjacent a target treatment site within a blood vessel, e.g., from a retrograde approach (not shown). A balloon or other occlusion member may be expanded to engage the wall of the vessel, and a therapeutic fluid may be introduced via the catheter into the target side, e.g., distal to or upstream from the balloon. The fluid may at least partially de-endothelialize the vessel wall, e.g., to cause fibrous growth that may strengthen the vessel wall and/or may occlude the vessel at the treatment site.

B. Delivery of De-Endothelialization Fluid Using an Implantable Device

Figure 47:
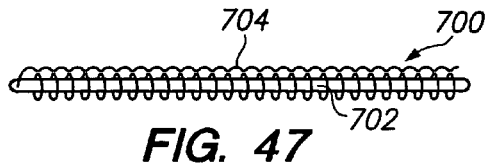
FIG. 47 is a side view of a de-endothelialization device including a fiber attached to an elongate core member.

De-endothelialization fluid 350 may also be delivered to an aneurysm or other body lumen using an implantable device, such as a vaso-occlusive device. FIG. 47 shows a de-endothelialization device 700 that may be used to deliver a de-endothelialization fluid or composition to an aneurysm or other body lumen. The de-endothelialization device 700 includes a core member 702 and a fiber 704 secured to the core member 702. The fiber 704 is capable of absorbing and/or retaining fluid, e.g., by capillary action. Alternatively, the fiber 704 may carry de-endothelialization agents that are chemically or physically attached to the fiber 704.

Figure 48:
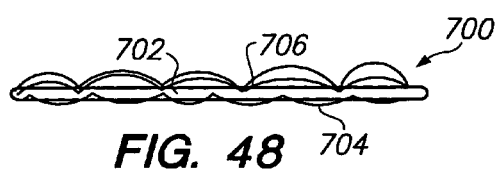
FIG. 48 is a side view of a variation of the de-endothelialization device of FIG. 47.
Figure 49:
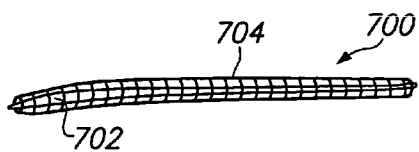
FIG. 49 is a side view of another variation of the de-endothelialization device of FIG. 47.

FIG. 48 shows a variation of the de-endothelialization device 700 in which the fiber 704 is substantially longitudinally oriented and is secured to the core member 702 at one or more locations 706 along a length of the core member 702. FIG. 49 shows another variation of the de-endothelialization device 700 in which one or more fibers 704 are arranged into a mesh that is secured to the core member 702. The fiber(s) 704 may be arranged in a variety of patterns and are not limited to those shown previously.

The core member 702 may be made from a variety of materials. In general, any of the materials discussed previously with reference to the core member 12 of FIG. 1 is also applicable the core member 702 of the de-endothelialization device 700. The core member 702 may also assume a variety of shapes. Any of the shapes discussed previously with reference to FIGS. 1-11 may also be used.

When using the de-endothelialization device 700, the de-endothelialization device 700 may be dipped into a de-endothelialization fluid, which may be absorbed and/or otherwise retained by the fiber 704 of the de-endothelialization device 700. The de-endothelialization device 700 may then be delivered to an aneurysm or other body lumen using any of the methods described previously with reference to FIGS. 12-15, or any conventionally known method. After the de-endothelialization device 700 contacts the endothelium of the aneurysm or other body lumen, the fluid 350 then causes the endothelium to be disrupted, as discussed previously.

It should be noted that instead of using the de-endothelialization device 700 described previously, a similar procedure may be completed using any implantable object, such as a vaso-occlusive device. In particular, a vaso-occlusive device may be dipped into de-endothelialization fluid, which may then adhere to a surface of the vaso-occlusive device by surface adhesion. The vaso-occlusive device, carrying the fluid, may then be delivered to an aneurysm or other body lumen.

Figure 50:
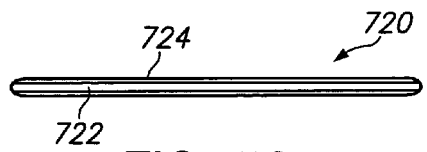
FIG. 50 is a cross-sectional side view of a de-endothelialization device including a coating containing a de-endothelializing compound therein.

FIG. 50 shows another de-endothelialization device 720 that includes a core member 722 and a coating 724 secured to the core member 722. The coating 724 is preferably secured to the core member 722 during manufacturing. However, the coating 724 may also be applied on the core member 722 by a user immediately before a procedure. The coating 724 may be applied to the core member 722, for example, by dipping the core member 722 into a solution. The coating 724 may contain similar de-endothelializing ingredients, such as a cytotoxic agent, as that of de-endothelialization fluids described above. When the de-endothelialization device 720 is placed within an aneurysm, a body temperature and/or a chemical reaction may be used to degrade or dissolve the coating 724 to release the de-endothelializing ingredients. When the endothelium of the aneurysm or other body lumen is contacted by the de-endothelializing ingredients, the endothelium is then disrupted.

Figure 51:
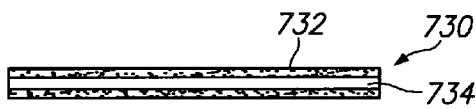
FIG. 51 is a cross-sectional side view of a de-endothelialization device including a hydrogel coating on an elongate core member.

De-endothelialization fluid 350 may also be delivered via a hydrogel coating. FIG. 51 shows a de-endothelialization device 730 having a hydrogel coating 732 coupled to a core member 734. The hydrogel coating 732 is capable of absorbing a desired amount of de-endothelialization fluid. Examples of hydrogels include gels formed from polysaccharides, mucopolysaccharides, polyaminoacids, proteins that support cell growth and healing, polyphosphazines, polyphosphoesters, polyethylene glycol, polyethylene oxide, polyvinyl alcohol, polyvinylpyrrolidone, polyethyloxazoline, polyethylene oxide-co-polypropyleneoxide block copolymers, PGA-PEG-PGA block copolymers, PGA-PEG diblock copolymers, acrylates, carboxy alkyl celluloses, partially oxidized cellulose, polymers and oligomers of glycolide and lactide, polylactic acid, polyesters of .alpha.-hydroxy acids, polylactones, polycaprolactones, polyanhydrides, polyorthoesters, polydioxanone, styrene, acrolein and combinations thereof. Other examples of hydrogels may also include gels formed from hyaluronic acid, dextran, heparin sulfate, chondroitin sulfate, heparin, agar, starch, alginate, fibronectin, gelatin, collagen, fibrin, pectins, albumin, ovalbumin, collagen-hydroxyethyl-methacrylate (HEMA); diacrylates, oligoacrylates, methacrylates, dimethacrylates, oligomethoacrylates, PEG-oligoglycolylacrylates, carboxymethyl cellulose, polyesters of lactic acid, polyesters of glycolic acid, poly(.alpha.-hydroxy) acids including polyglycolic acid, poly-DL-lactic, poly-L-lactic acid, and terpolymers of DL-lactide and glycolide, .epsilon.-caprolactone, .epsilon.-caprolactone copolymerized with polyesters, poly(.epsilon.-caprolactone), poly(.delta.-valerolactone), poly(gammabutyrolactone), and combinations thereof. When using the de-endothelialization device 730, the de-endothelialization device 730 is first dipped into de-endothelialization fluid. Due to the absorptive characteristic of the hydrogel coating 732, the hydrogel coating 732 absorbs the fluid and retains the fluid within the coating 732.

The endothelialization device 730 may then be delivered to an aneurysm or other body lumen using any of the methods discussed previously. Once situated inside the sac of the aneurysm or at the site of another body lumen, the fluid may diffuse from the hydrogel coating 732 and contact the endothelium of the aneurysm or other body lumen to disrupt the endothelium.

Although several embodiments and methods of de-endothelializing an aneurysm or other body lumen have been described, it should be noted that one or more of the above described embodiments may be combined with another. For example, the de-endothelialization device 10 described with reference to FIGS. 1-11 may also be heated and/or dipped into de-endothelialization fluid to enhance its de-endothelialization properties. Also, the de-endothelialization device 300 described previously with reference to FIG. 30 can also include an abrasive element 14, such as that shown in FIG. 1, to enhance its de-endothelialization property. Combination of other embodiments described previously may also be used.

Furthermore, although the embodiments have been discussed with reference to treating aneurysms, the scope of the invention should not be so limited. For example, any of the above described embodiments may also be used to de-endothelialize vascular tissue for treating arteriovenous malformations (AVMs), arteriovenous fistulas (AVFs), or other vascular conditions. Other bodily tissues may also be de-endothelialized for treatment of various medical conditions, such as tumors, using any of the above discussed devices and/or methods.

Thus, although several preferred embodiments have been shown and described, it would be apparent to those skilled in the art that many changes and modifications may be made thereto without departing from the scope of the invention, which is defined by the following claims and their equivalents.

What is claimed is:

1. A method for disrupting an endothelium of a wall of a treatment site adjacent a body lumen, comprising:
   introducing a tubular member into the body lumen until a distal end of the tubular member is located within the treatment site;
   sealing the treatment site from the body lumen; and
   damaging the endothelium of the wall of the treatment site by delivering a cell-disrupting cytotoxic agent comprising a hypotonic fluid via a lumen of the tubular member into the treatment site, such that the cell-disrupting hypotonic fluid contacts the wall of the treatment site,
   wherein the treatment site comprises an aneurysm, an arterio-venous malformation, or a fistula.

2. The method of claim 1, further comprising advancing a delivery device into the body lumen until a distal end of the delivery device is adjacent the treatment site, and wherein the tubular member is introduced from within the delivery device into the treatment site.

3. The method of claim 2, wherein a sealing member is carried by the tubular member or the delivery device, and wherein the sealing member is expandedable.

4. The method of claim 3, wherein the sealing member comprises an annular shaped member comprising an outer wall and a passage extending therethrough, and wherein the annular shaped member is positioned such that the outer wall is disposed adjacent the treatment site to substantially seal the treatment site and the passage is disposed coaxially within the body lumen to allow continued fluid flow along the body lumen.

5. The method of claim 2, further comprising aspirating fluid from within the treatment site after the cell-disrupting fluid is delivered into the treatment site.

6. The method of claim 1, wherein the tubular member comprises a coil extending from the distal end into the treatment site, the coil dispersing the cell-disrupting fluid delivered into the treatment site in a desired pattern within the treatment site.

7. The method of claim 1, wherein the tubular member comprises a balloon carried on the distal end thereof, and wherein the cell-disrupting fluid is delivered via the balloon.

8. The method of claim 7, wherein the balloon comprises one or more openings extending through a wall of the balloon and communicating with an interior of the balloon, and wherein the cell-disrupting fluid is delivered to contact the wall of the treatment site through the one or more openings.

9. The method of claim 8, wherein the step of delivering the cell-disrupting fluid into the treatment site comprises introducing the cell-disrupting fluid into the interior of the balloon, thereby expanding the balloon until the one or more openings expand sufficiently to allow the cell-disrupting fluid to exit from the interior of the balloon through the one or more openings.

10. The method of claim 7, wherein the balloon comprises a delivery lumen formed within a wall of the balloon and wherein the cell-disrupting fluid is delivered into the treatment site through the delivery lumen.

11. A method for disrupting an endothelium of a wall of a treatment site adjacent a body lumen, comprising:
   introducing a tubular member into the body lumen until a distal end of the tubular member is located adjacent the treatment site, the distal end carrying an annular shaped member;
   expanding the annular shaped member until an outer wall of the annular shaped member substantially seals the treatment site from the body lumen, the annular shaped member comprising a passage extending therethrough to allow continued fluid flow along the body lumen; and
   damaging the endothelium of the wall of the treatment site by delivering a cell-disrupting cytotoxic agent comprising a hypotonic fluid into the treatment site, such that the cell-disrupting hypotonic fluid contacts the wall of the treatment site,
   wherein the treatment site comprises an aneurysm, an arterio-venous malformation, or a fistula.

12. The method of claim 11, wherein the annular shaped member comprises one or more openings in the outer wall, and wherein the cell-disrupting fluid is delivered into the treatment site through the one or more openings.

13. The method of claim 11, wherein the cell-disrupting fluid is delivered via a second tubular member comprising a distal end introduced into the treatment site, the second tubular member positioned adjacent the annular shaped member such that the outer wall substantially engages the second tubular member as the annular shaped member is expanded.

14. A method for treating a treatment site adjacent a body lumen, the method comprising:
   introducing a tubular member into the body lumen until a distal end of the tubular member is located within the treatment site;
   substantially sealing the treatment site from the body lumen;
   aspirating fluid from within the treatment site;

damaging an endothelium of a wall of the treatment site by delivering a cell-disrupting cytotoxic agent comprising a hypotonic fluid via the tubular member into the treatment site to contact and at least partially de-endothelialize the endothelium of the wall of the treatment site; and aspirating the cell-disrupting hypotonic fluid from the treatment site, wherein the treatment site comprises an aneurysm, an arterio-venous malformation, or a fistula.

15. The method of claim 14, wherein the treatment site is substantially sealed from the body lumen by expanding an occlusion member carried on the distal end of the tubular member to engage an entrance into the treatment site.

16. The method of claim 15, further comprising collapsing the occlusion member after the cell-disrupting hypotonic fluid is aspirated from the treatment site.

17. The method of claim 14, wherein the treatment site is substantially sealed from the body lumen by introducing an occlusion member into the body lumen until the occlusion member is adjacent the treatment site and expanding the occlusion member to substantially seal the treatment site.

18. The method of claim 14, wherein the step of aspirating fluid from the treatment site comprises flushing the treatment site with fluid and aspirating excess fluid from the treatment site.

19. The method of claim 18, wherein the treatment site is flushed and aspirated substantially simultaneously.

20. The method of claim 14, wherein the cell-disrupting hypotonic fluid causes at least one of the following to occur within the treatment site: cellular lysis, disruption of cellular or intercellular adhesions, and disruption of cellular function.

21. The method of claim 14, wherein the treatment site comprises the aneurysm.

22. The method of claim 21, wherein the body lumen comprises a cerebral artery.

23. The method of claim 14, wherein the treatment site comprises the arterio-venous malformation, and wherein the body lumen comprises an artery communicating with the arterio-venous malformation.

24. The method of claim 23, wherein the step of substantially sealing the treatment site comprises expanding an occlusion member within the artery to substantially isolate the artery from the arterio-venous malformation.

25. The method of claim 24, wherein a vein communicates with the arterio-venous malformation, and wherein the step of substantially sealing the treatment site further comprises expanding an occlusion member within the vein to substantially isolate the vein from the arterio-venous malformation.

26. The method of claim 14, wherein the treatment site comprises the fistula or a tumor-feeding vessel, and wherein the body lumen comprises a blood vessel communicating with the fistula or tumor-feeding vessel.

27. The method of claim 2, wherein the cell-disrupting hypotonic fluid is aspirated from the treatment site via a lumen in the delivery device.

28. The method of claim 27, the tubular member further comprising a coiled member engaged to the distal end of the tubular member, and the coiled member disperses the cell-disrupting hypotonic fluid in the treatment site.

29. The method of claim 28, wherein the coiled member is deployed from the tubular member into the treatment site.

30. The method of claim 14, further comprising advancing a delivery device into the body lumen until a distal end of the delivery device is adjacent the treatment site, and wherein the tubular member is introduced from within the delivery device into the treatment site.

31. The method of claim 30, wherein the treatment site is substantially sealed from the body lumen by the delivery device.

32. The method of claim 30, wherein the cell-disrupting hypotonic fluid is aspirated from within the treatment site via a lumen in the delivery device.

33. The method of claim 30, wherein the tubular member further comprises a coiled member engaged to the distal end of the tubular member, and the coiled member disperses the cell-disrupting hypotonic fluid in the treatment site.

34. The method of claim 33, wherein the coiled member is deployed from the tubular member into the treatment site.

* * * * *